US009161681B2

(12) United States Patent
Galstian et al.

(10) Patent No.: US 9,161,681 B2
(45) Date of Patent: Oct. 20, 2015

(54) MOTIONLESS ADAPTIVE STEREOSCOPIC SCENE CAPTURE WITH TUNEABLE LIQUID CRYSTAL LENSES AND STEREOSCOPIC AUTO-FOCUSING METHODS

(75) Inventors: Tigran Galstian, Québec (CA); Peter P Clark, Boxborough, MA (US); Suresh Venkatraman, Los Altos, CA (US)

(73) Assignee: LENSVECTOR, INC., Mountain View, CA (US)

( * ) Notice: Subject to any disclaimer, the term of this patent is extended or adjusted under 35 U.S.C. 154(b) by 800 days.

(21) Appl. No.: 13/311,377

(22) Filed: Dec. 5, 2011

(65) Prior Publication Data

US 2012/0140037 A1    Jun. 7, 2012

Related U.S. Application Data

(60) Provisional application No. 61/420,122, filed on Dec. 6, 2010.

(51) Int. Cl.
*H04N 13/00* (2006.01)
*A61B 1/04* (2006.01)
*H04N 13/04* (2006.01)
*G03B 3/00* (2006.01)
*G03B 13/00* (2006.01)
*G06K 9/00* (2006.01)
*G06K 9/40* (2006.01)
(Continued)

(52) U.S. Cl.
CPC .............. *A61B 1/00193* (2013.01); *G02B 3/14* (2013.01); *G02B 27/22* (2013.01); *H04N 13/0239* (2013.01); *H04N 13/0242* (2013.01)

(58) Field of Classification Search
CPC ...... A61B 1/00193; G02B 3/14; G02B 27/22; H04N 13/0242; H04N 13/0239

USPC ........................................................... 348/45
See application file for complete search history.

(56) References Cited

U.S. PATENT DOCUMENTS

| 5,793,900 A * | 8/1998 | Nourbakhsh et al. ......... 382/263 |
| 2004/0169922 A1 * | 9/2004 | Wilson et al. ................. 359/462 |

(Continued)

FOREIGN PATENT DOCUMENTS

| WO | WO 2009/146529 A1 | 12/2009 |
| WO | WO 2009/146530 A1 | 12/2009 |
| WO | WO 2010/022080 A1 | 2/2010 |

OTHER PUBLICATIONS

A.F.Naumov et al., Control optimization of spherical modal liquid crystal lenses, Optics Express, pp. 344-352, Apr. 26, 1999, vol. 4, No. 9.

*Primary Examiner* — Hee-Yong Kim
(74) *Attorney, Agent, or Firm* — J-Tek Law PLLC; Jeffrey D. Tekanic; Scott T. Wakeman

(57) ABSTRACT

A motionless adaptive focus stereoscopic scene capture apparatus employing tunable liquid crystal lenses is provided. The apparatus includes at least two image sensors preferably fabricated as a monolithic stereo image capture component and at least two corresponding tunable liquid crystal lenses preferably fabricated as a monolithic focus adjustment component. Using a variable focus tunable liquid crystal lens at each aperture stop provides constant magnification focus control. Controlled spatial variance of a spatially variant electric field applied to the liquid crystal of each tunable liquid crystal lens provides optical axis shift enabling registration between stereo images. A controller implements coupled auto-focusing methods employing multiple focus scores derived from at least two camera image sensors and providing multiple tunable liquid crystal lens drive signals for synchronous focus acquisition of a three dimensional scene. Wafer manufacture provides a compact stereoscopic image capture apparatus for endoscopic surgery, optical inspection and entertainment applications.

29 Claims, 21 Drawing Sheets

(51) Int. Cl.
*A61B 1/00* (2006.01)
*G02B 3/14* (2006.01)
*G02B 27/22* (2006.01)
*H04N 13/02* (2006.01)

(56) References Cited

U.S. PATENT DOCUMENTS

| | | | |
|---|---|---|---|
| 2005/0054910 A1* | 3/2005 | Tremblay et al. | 600/411 |
| 2007/0139333 A1 | 6/2007 | Sato et al. | |
| 2007/0229754 A1 | 10/2007 | Galstian et al. | |
| 2008/0309835 A1* | 12/2008 | Kuba | 349/1 |
| 2009/0185760 A1* | 7/2009 | Okada et al. | 382/299 |
| 2009/0213321 A1 | 8/2009 | Galstian et al. | |
| 2009/0245074 A1 | 10/2009 | Tseng | |
| 2010/0039532 A1 | 2/2010 | Galstian et al. | |
| 2010/0194865 A1* | 8/2010 | Kusada | 348/52 |
| 2011/0073656 A1* | 3/2011 | Detwiler et al. | 235/462.41 |
| 2011/0181797 A1* | 7/2011 | Galstian et al. | 349/2 |
| 2012/0014559 A1* | 1/2012 | Suehling et al. | 382/103 |
| 2012/0019761 A1 | 1/2012 | Nystrom et al. | |

* cited by examiner

Scene of Interest

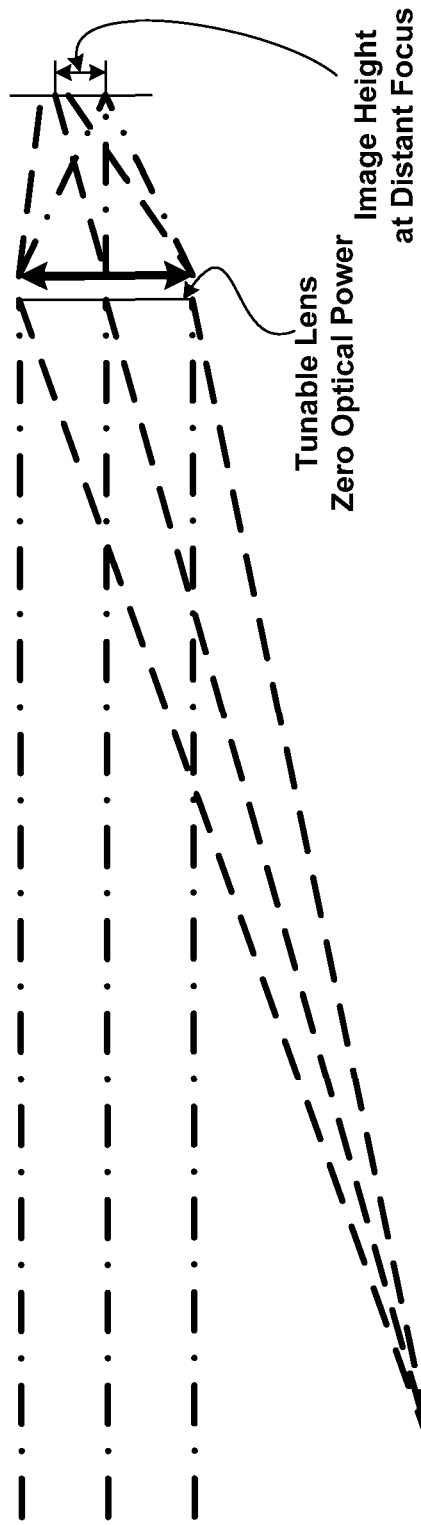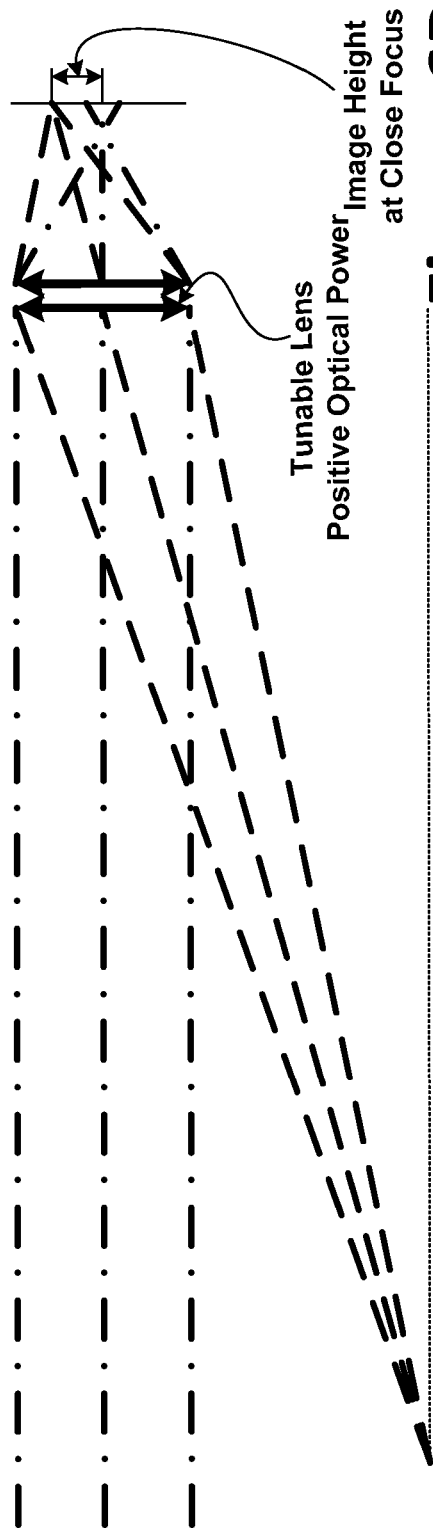

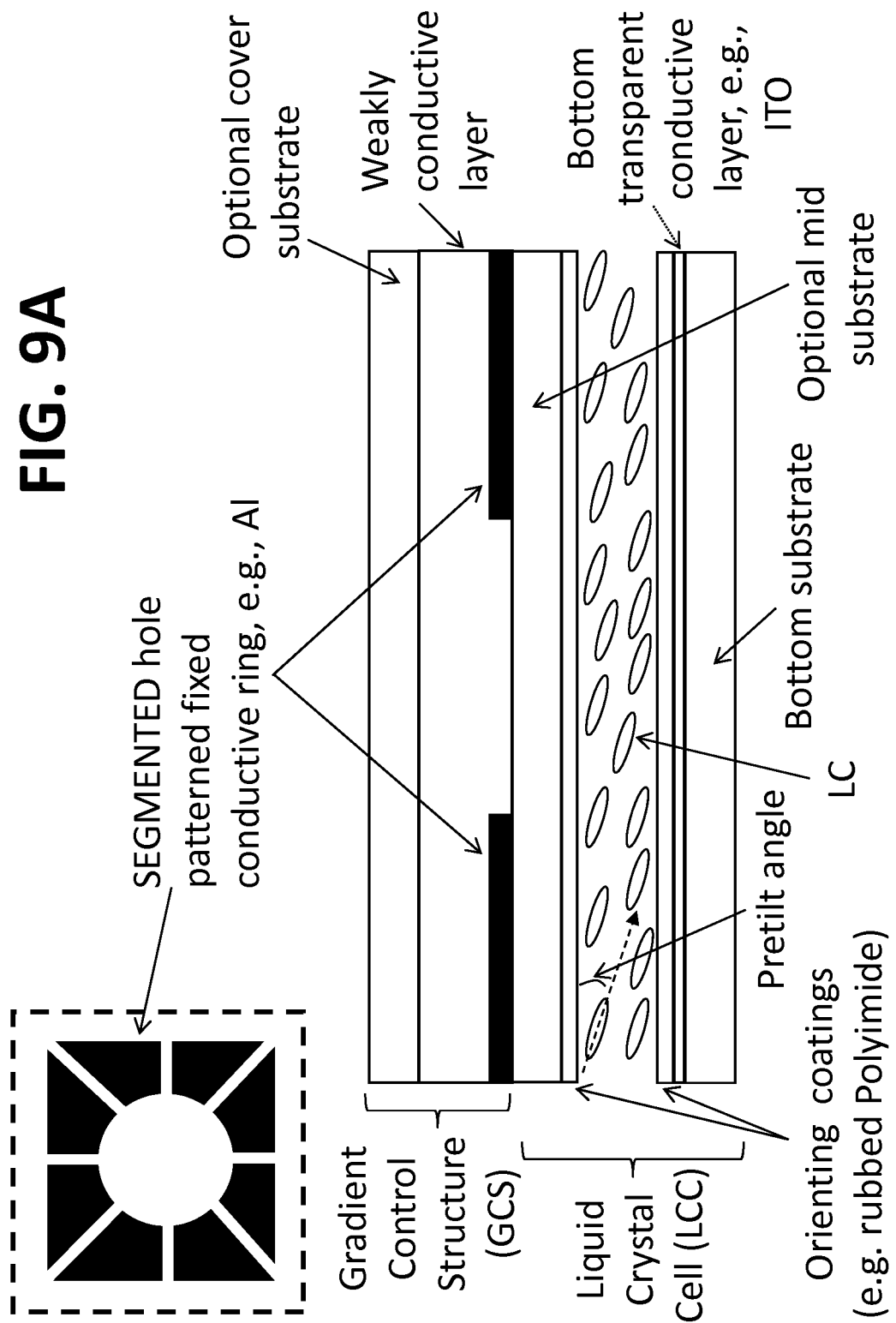

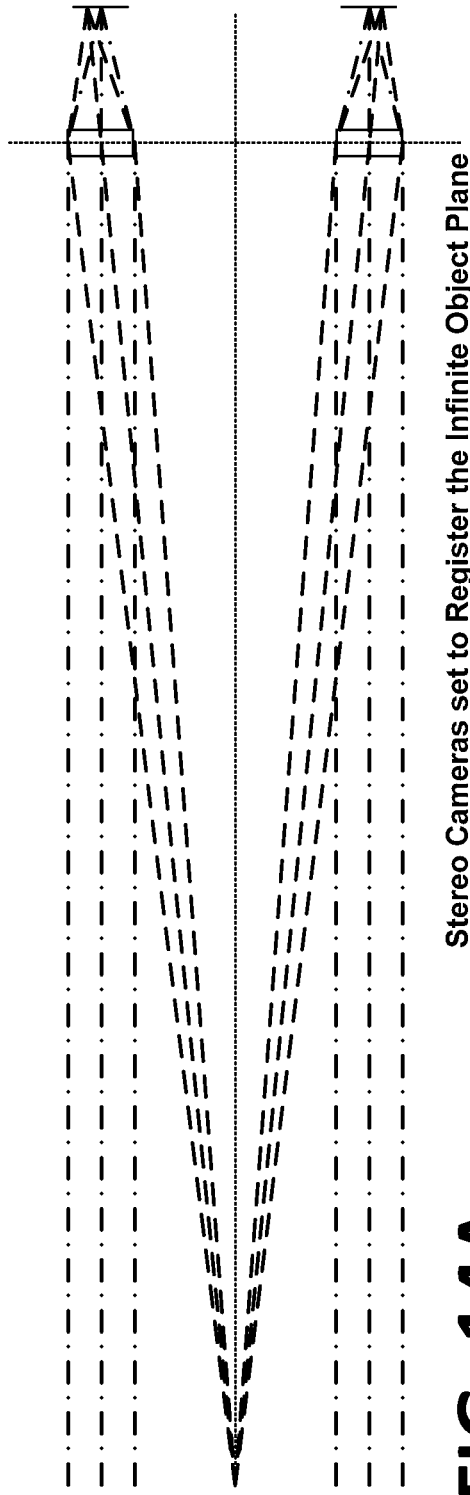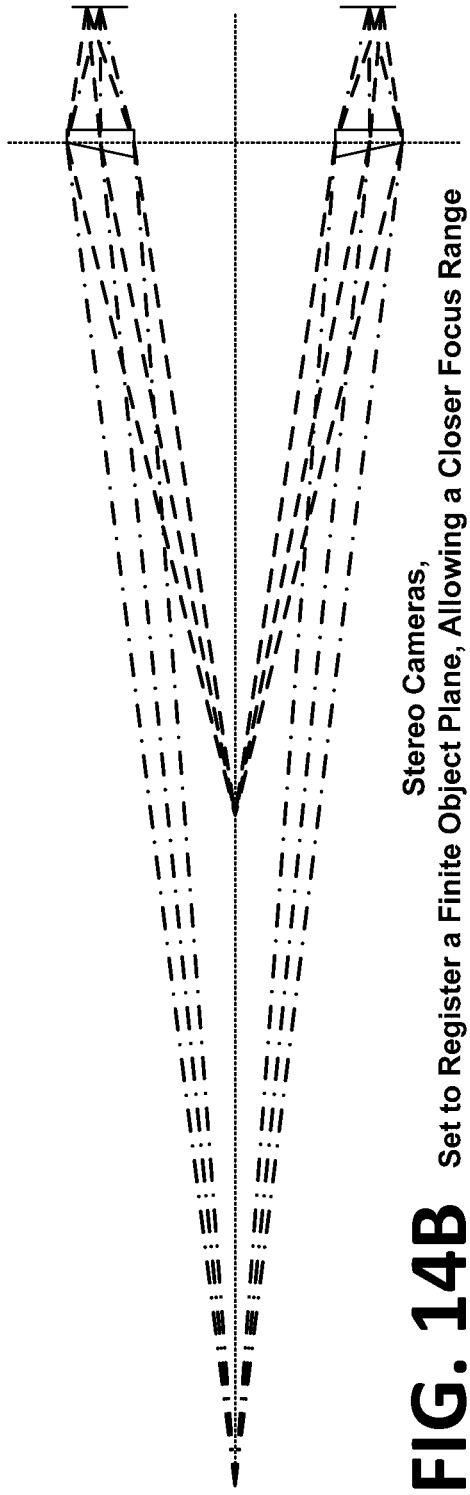
FIG. 14A  Stereo Cameras set to Register the Infinite Object Plane
FIG. 14B  Stereo Cameras, Set to Register a Finite Object Plane, Allowing a Closer Focus Range

MOTIONLESS ADAPTIVE STEREOSCOPIC SCENE CAPTURE WITH TUNEABLE LIQUID CRYSTAL LENSES AND STEREOSCOPIC AUTO-FOCUSING METHODS

RELATED APPLICATIONS

This application claims priority from U.S. Provisional Application Ser. No. 61/420,122, filed on Dec. 6, 2010, the entirety of which is incorporated herein by reference.

TECHNICAL FIELD

This invention relates to digital imaging systems, and in particular to adaptive focus stereoscopic imaging systems and stereoscopic auto-focusing methods.

BACKGROUND

In a variety of fields, there is a growing need for capturing and/or projecting three-dimensional (3D) images. Specific applications range from medicine to entertainment. A 3D effect is perceived by presenting different images of a scene to the left and right eyes of a viewer. The center of each camera's entrance pupil is referred to as a point of view. The typical approach for 3D (stereoscopic) recording uses two or more spatially separated cameras that simultaneously record real-time changes of the same scene from different points of view. The 3D effect is dependent upon the different points of view of the multiple cameras. The spatial separation of the multiple cameras may include positional differences (shift) and angular differences (tilt). Positional differences account for parallax. Angular differences account for the angular direction of incident light, with respect to the scene, from which a camera captures the scene. This is also referred to as line of sight.

An example of such an arrangement is illustrated schematically in FIG. 1. Two spatially separated cameras 10, 12 have different respective positions and tilts relative to a scene of interest. The central optical axis 14 of camera 10 and the central optical axis 16 of camera 12 typically intersect at the location of the scene of interest such that the cameras provide two different simultaneous views of the scene from two points of view. As indicated in FIG. 1, the two cameras have a relative operational lateral shift d and a relative operational tilt a.

With a dual camera system such as illustrated in FIG. 1, it is necessary to maintain a good focus for each camera in order for the 3D image captured to have a good focus. For scenes having a dynamic character (image object motion in space over time) and/or a natural 3D (volumetric) profile, auto-focus capability and/or variable focus capability becomes necessary.

In conventional variable focus systems, focusing is achieved through the use of mechanically moving optical elements, typically spherical lenses. Typical optical element displacement is provided by stepper motor or voice coil drive arrangements.

Conventional 3D capture therefore requires mechanically moving optical elements for each camera. FIG. 2 illustrates a prior art dual camera system based on the dual camera system illustrated in FIG. 1 with cameras 10 and 12 directed at a scene of interest. A mechanical focus adjustment mechanism is employed for each camera, mechanism 18 being associated with camera 10 and mechanism 20 being associated with camera 12. Each focus adjustment mechanism must be individually actuated to provide a good focus of the scene which, as indicated in FIG. 2, is at a distance D from cameras 10, 12.

It has been found that time-synchronization between multiple mechanical drive arrangements for optical element displacement is very difficult, for example due to mechanical movement, ringing and other inertial effects. Time-synchronization affects dual camera systems employed in a variety of applications.

A significant drawback of conventional focusing systems is that such mechanical focusing devices tend to be bulky and relatively expensive making them impractical/unsuitable for many applications, and in particular do not lend themselves well to miniaturization.

In addition to time synchronization difficulties, further undesirable problems arise in conventional focusing systems if the cameras are not perfectly telecentric, as the mechanical optical element displacement employed to adjust focus also changes image magnification. The following examples show such image magnification change with relative mechanical displacement between a conventional optical lens element and an image sensor. For ease of understanding, the optical lens element is shown stationary and the image sensor shown moving. Such arrangement is not uncommon in practical implementations. For certainty, the following treatment is dependent only the relative motion between the optical lens element and the image sensor and applies in an equal way to the more conventional implementation wherein the image sensor is stationary and the optical lens element is displaced with respect to the image sensor.

FIG. 3 illustrates a ray diagram of a conventional non-telecentric imaging system model having variable focus achieved by moving the image sensor (camera) with respect to the optical lens element. Providing focus control via displacement between the image sensor and a non-telecentric optical lens arrangement results in a higher magnification for objects imaged at close focus than for objects imaged at distant focus. As magnification of an imaged object on the image sensor is given by the ratio between the imaged object height and the tangent of the field angle, the non-zero chief ray angle causes different magnifications for the same imaged object at different image sensor locations. In practice, optical element displacement relative to the image sensor requires precise moving parts. A person of skill in the art would understand that FIG. 3 is idealized, in practice the optical lens shown is a compound optical element including a multitude of optical components including, but not limited to spherical or aspherical glass, crystal or plastic lens elements of considerable thickness. Miniaturization of such mechanical displacement focus systems is very difficult due to material limitations of glass lens elements.

Moreover, for dual camera 3D imaging, where each camera typically requires a different focus adjustment setting, magnification change with focus is further undesirable because the resulting image size differences (due to magnification) and image field extent differences (more or less of the scene fits in a same size image frame as viewed from the other point of view) affect image registration between the two images in the stereoscopic pair. Lack of registration is disturbing to a viewer (user). Moreover, with the two imaging channels being focused differently, magnification differences could affect stereo fusing (blending images).

FIG. 4 illustrates a ray diagram of a conventional telecentric imaging system model having variable focus achieved by moving the image sensor (camera) with respect to a glass lens. Providing focus control via displacement between the image sensor and a telecentric optical lens arrangement results in constant magnification for all imaged objects because the chief ray angle remains zero for all image distances. However, besides requiring precise moving parts for precise optical element displacement relative to the image sensor, extra conventional optical lens complexity is required to achieve such telecentric design. That is, the compound optical element employed has a higher complexity typically requiring more glass lenses which considerably increase thickness. Miniaturization of such mechanical displacement focusing systems and complex optical lens elements is very difficult due to material limitations.

There is a need to improve focusing in dual camera systems.

SUMMARY

It is an object of the present proposed solution to provide efficient control over the movement of the focus of a tunable liquid crystal lens.

It has been discovered that efficient control of an electric field using a frequency dependent material or a weakly conductive layer can be performed using a segmented electrode to give control over the movement of the focus of the resulting tunable liquid crystal lens.

It has been discovered that the optical axis of a tunable liquid crystal lens can be moved using a controllable heat source affecting at least one of the electric field modulation and the liquid crystal.

It has been discovered that the optical axis of a tunable liquid crystal lens can be moved/redirected using a controllable pressure source affecting substrates of the liquid crystal lens structure. A suitable pressure source may be provided by piezoelectric cell actuated by a drive signal or by a fluid-filled cell actuated by a heat source.

Shifting or changing the optical axis in a lens forming part of a lens arrangement for a camera is useful for: lens position adjustment to achieve alignment with other lens elements for image registration to provide parallax for stereoscopic applications; angular lens adjustment of a lens (pitch and pan). Such, optical axis adjustment mechanism can be set once, adjusted prior to image acquisition or dynamically adjusted during image acquisition, as required for the given stereoscopic scene capture applications as the distance to the scene is varied and as the focus is varied.

In accordance with an aspect of the proposed solution there is provided a digital imaging apparatus for capturing an image of a scene, the apparatus comprising at least one camera having an aperture stop, each camera including an image capture subsystem a fixed distance away from the aperture stop; and a focusing component including a variable optical power tunable liquid crystal lens corresponding to said camera, said liquid crystal lens being located substantially at the aperture stop of said corresponding camera, said image capture subsystem being located at a fixed distance away from said aperture stop and said corresponding liquid crystal lens being located substantially at the aperture stop providing focus adjustment via tunable liquid crystal lens optical power adjustment at fixed magnification.

In accordance with another aspect of the proposed solution there is provided a stereoscopic imaging apparatus for capturing a stereoscopic image of a three dimensional scene, the apparatus comprising: a plurality of cameras; a focusing component including a variable optical power tunable liquid crystal lens corresponding to each camera of said a plurality of cameras; and a common focus control component configured to provide stereoscopic focus acquisition by focusing each liquid crystal lens on said scene at a scene distance away from said apparatus.

In accordance with a further aspect of the proposed solution there is provided a stereoscopic imaging apparatus for capturing a stereoscopic image of a three dimensional scene, the apparatus comprising: a plurality of cameras; a focusing component including a variable optical power tunable liquid crystal lens corresponding to each camera of said a plurality of cameras, said focusing component providing stereoscopic focus acquisition by focusing each liquid crystal lens on said scene at a scene distance away from said apparatus; and at least one of a pair of said tunable liquid crystal lenses including an optical axis orientation adjustment component providing a relative angle of view adjustment between said pair of liquid crystal lenses as a function of said scene distance.

In accordance with a further aspect of the proposed solution there is provided a stereoscopic imaging apparatus for capturing a stereoscopic image of a three dimensional scene, the apparatus comprising: a plurality of cameras; a focusing component including a variable optical power tunable liquid crystal lens corresponding to each camera of said a plurality of cameras, each variable optical power tunable liquid crystal lens having electrical control characteristics; and a common tunable liquid crystal electrical control component for at least two tunable liquid crystal lenses having matched electrical control characteristics.

In accordance with a further aspect of the proposed solution there is provided an endoscopic apparatus for stereoscopic image acquisition.

In accordance with a further aspect of the proposed solution there is provided a differential focus stereoscopic effect enhancement via an arrangement employing differently focused lenses at different magnification and good left-right registration.

In accordance with yet another aspect of the proposed solution there is provided a coupled auto-focusing method for stereoscopic focus acquisition of a stereoscopic image of a three dimensional scene, the method comprising using at least two images to generate a focus score.

BRIEF DESCRIPTION OF THE DRAWINGS

The invention will be better understood by way of the following detailed description of embodiments of the invention with reference to the appended drawings, in which:

FIGS. 6A and 6B are a schematic diagrams showing ray diagrams of half of a dual camera system for capturing a three dimensional image of a scene in accordance with an embodiment of the proposed solution;

FIG. 9A is a schematic diagram showing a side sectional view of a tunable liquid crystal lens with an inset top view of a segmented top electrode according to an embodiment in which a frequency dependent material is above the segmented, hole patterned electrode;

FIGS. 14a, 14b and 14c are schematic diagrams illustrating methods of stereoscopic effect enhancement in accordance with the proposed solution;

DETAILED DESCRIPTION

Stereoscopic imaging a 3D scene depends upon the acquisition system and the display system. The following three parameters are important:

1) Angular magnification (at the point of view):

$Ma$=angular extent of the displayed scene/angular extent of the recorded scene

2) Pupil distance magnification (from multiple points of view):

$Me$=pupil separation of the viewer's eyes/pupil separation d of the two cameras 3) Apparent distance of the infinite object plane: Z'inf.

Changing these parameters can change the displayed space: angular magnification (lateral magnification) and pupil distance magnification (depth magnification) can change. If $Ma$=1, $Me$=1, Z'inf=infinity, then the world is reproduced as it is. Depth reproduction will be non-linear if Z'inf is not (effectively) infinity (see examples below).

Unlike viewer's eyes, display systems are generally fixed focus, in the sense that, a 3D video display always presents its images in the plane of the display. Closer objects or distant objects are all viewed by a viewer at the distance of the display, where depth is conveyed by the convergence required to fuse the left and right images. The difference between viewing a 3D display and viewing the real world is that the viewer's eyes do not have to change focus. The 3D display system gives a viewer the perception of depth by employing the convergence angle of the viewer's eyes at constant accommodation (focus setting). Surprisingly, this is not usually noticed by the observer.

However, for close scenes including macro imaging, near object imaging using telescopic lenses, and for poorly lit scenes requiring use of large apertures, the 3D stereoscopic image acquisition system, like any camera, may need to focus on an object of interest in the scene whether it is near or far. For such scenes, other parts of the acquired images may be out of focus (limited depth of field), for example a relatively distant background may be blurred for a camera system focused on a relatively near object through a wide aperture/telescopic lens. The viewer may perceive the blurry background as distant, but he/she will not be able to focus sharply on it.

Figure 1:
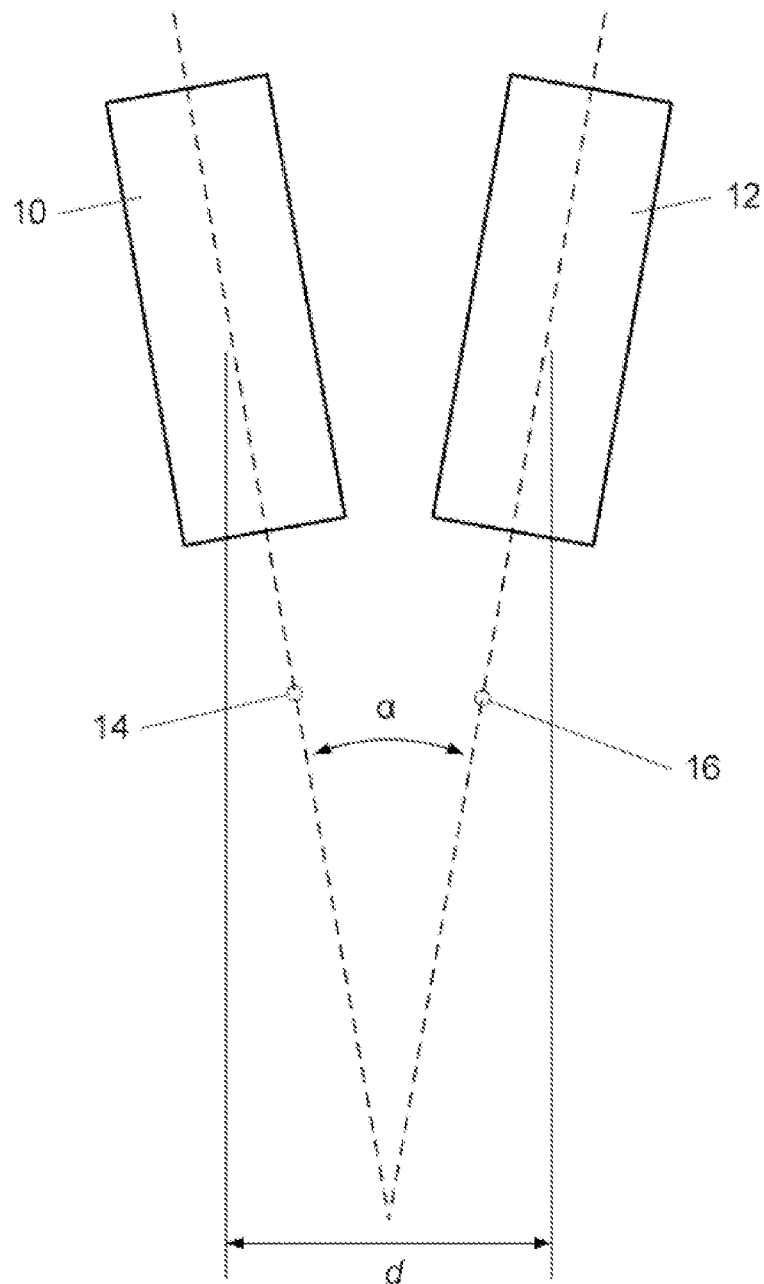
FIG. 1 is a schematic diagram showing a prior art dual camera system for capturing a three dimensional image of a scene.
Figure 2:
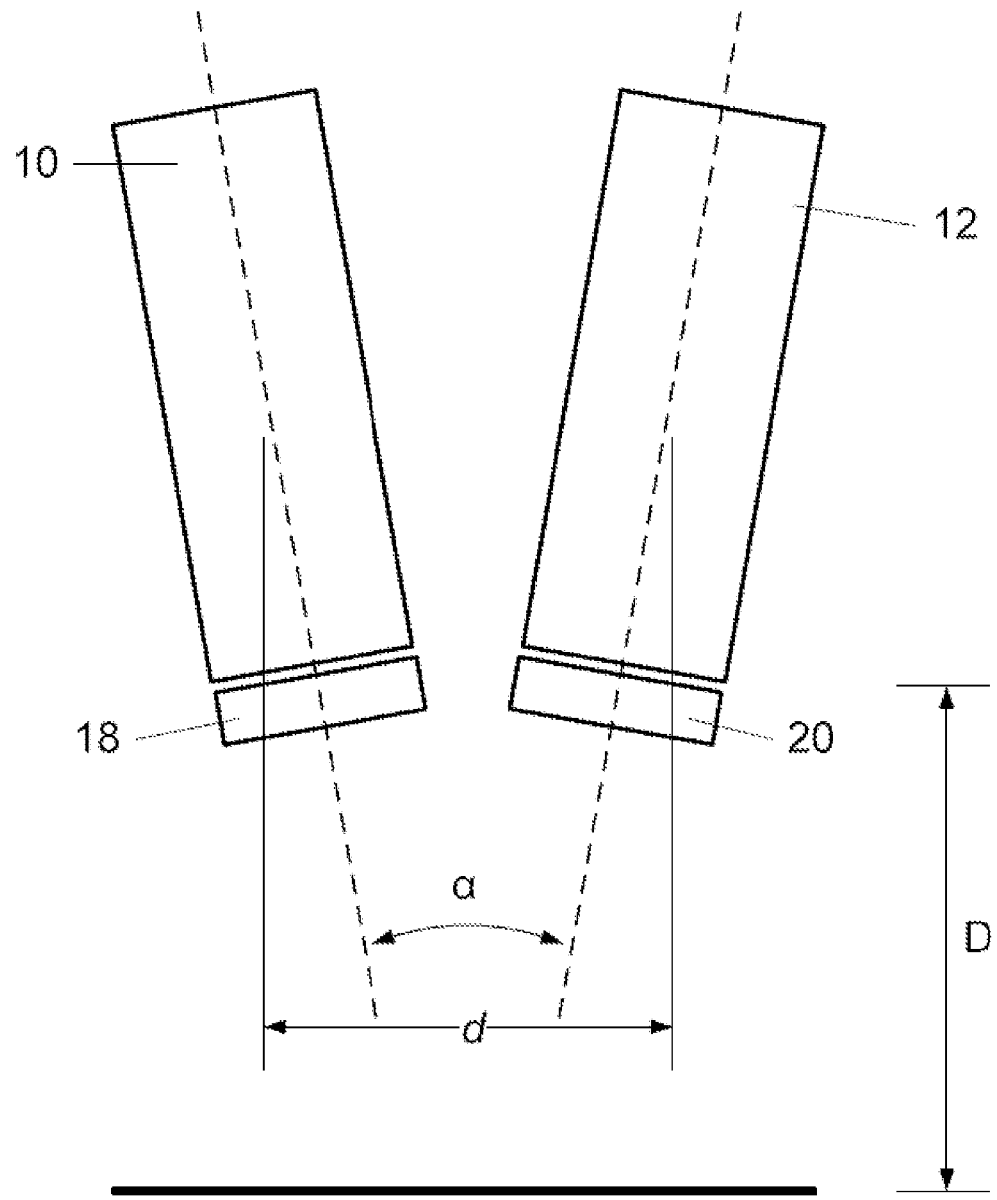
FIG. 2 is another schematic diagram showing a prior art dual camera system having focus control for capturing a three dimensional image of a scene.
Figure 3:
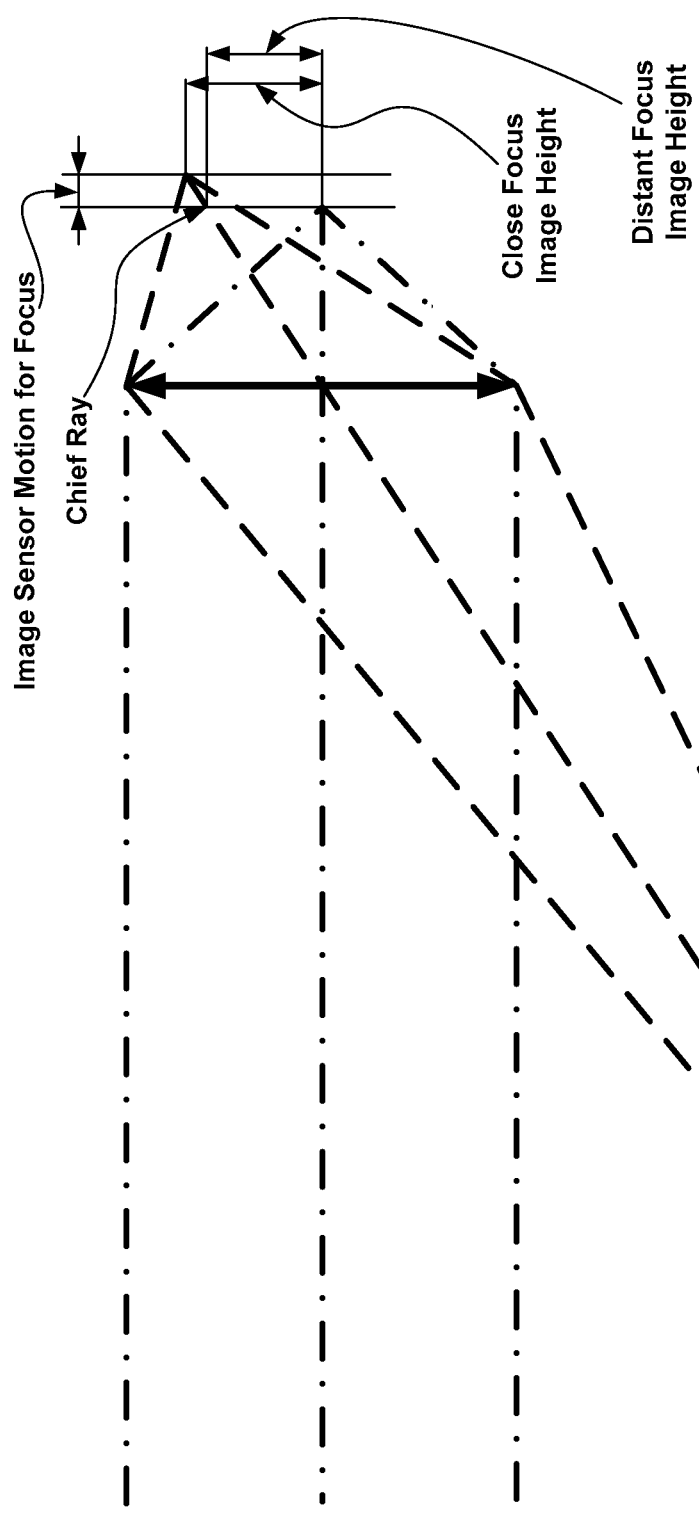
FIG. 3 is a schematic diagram showing a prior art ray diagram of a conventional imaging system having variable focus.
Figure 4:
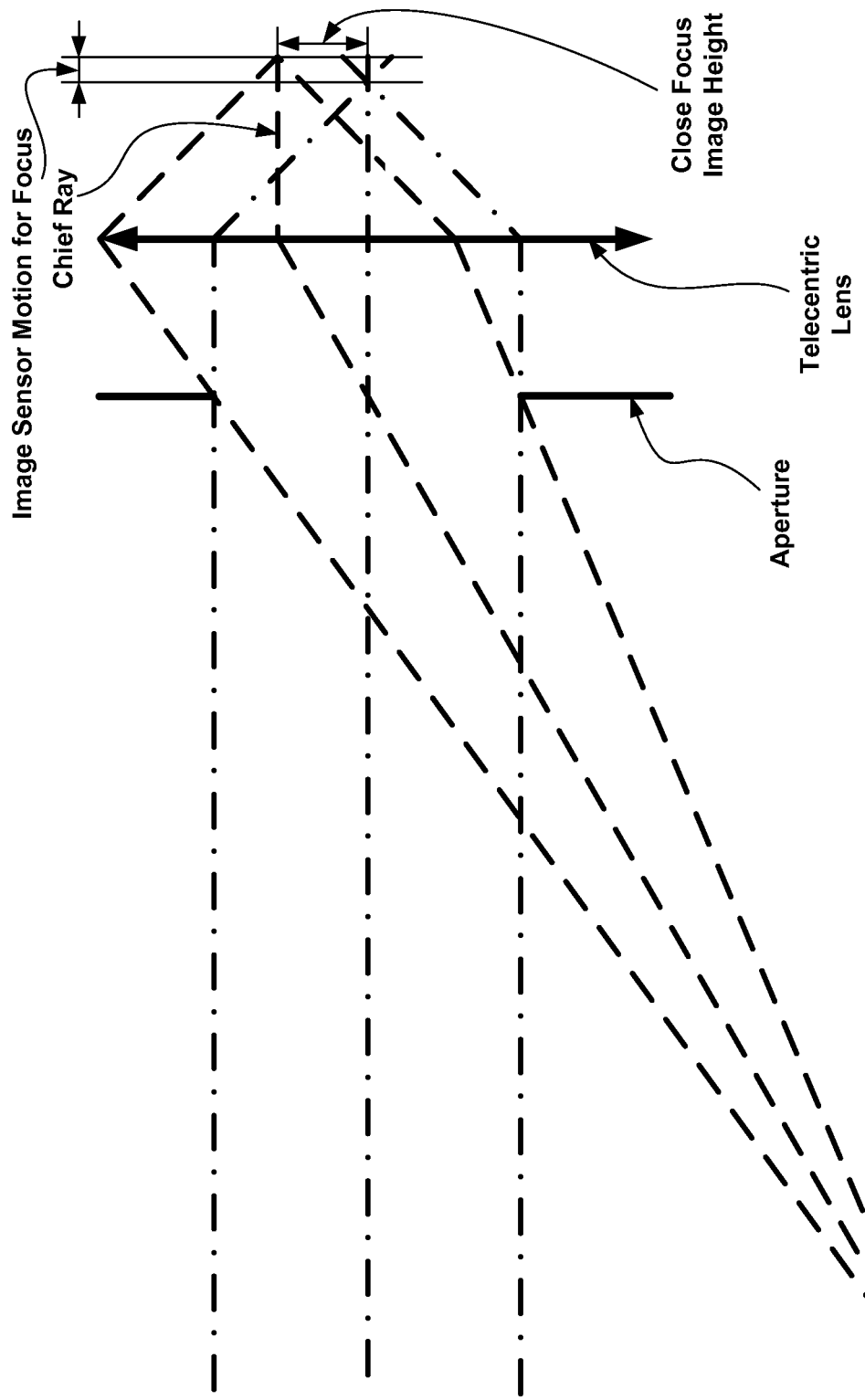
FIG. 4 is another schematic diagram showing another prior art ray diagram of another conventional imaging system having variable focus.
Figure 5:
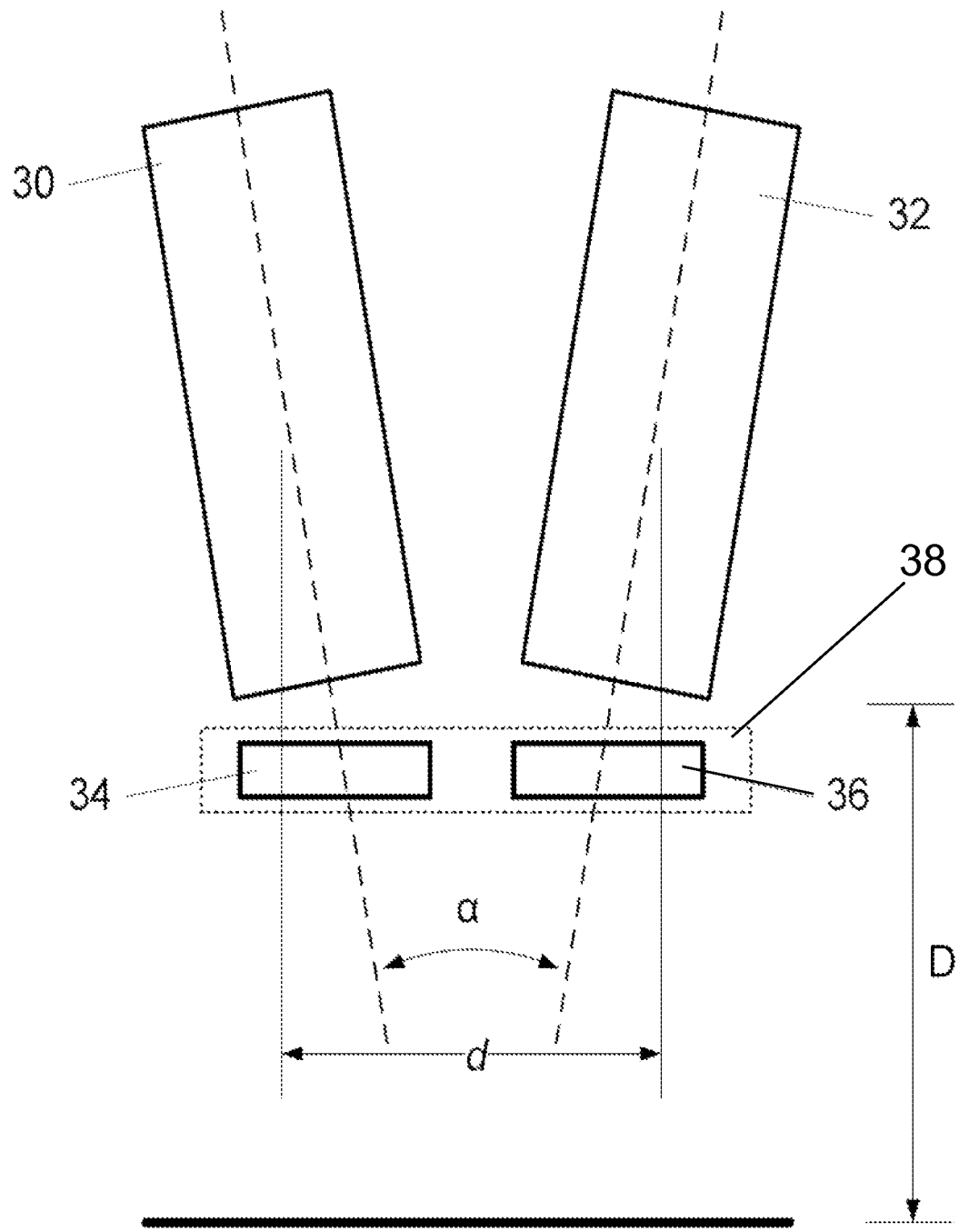
FIG. 5 is a schematic diagram showing a dual camera system for capturing a three dimensional image of a scene in accordance with an embodiment of the proposed solution.

FIG. 5 schematically illustrates a first embodiment of a stereoscopic image capture system in accordance with the proposed solution. Two cameras 30, 32, having a relative lateral shift d and angular tilt a, are directed toward a scene of interest, and each is at a distance of D from the scene of interest. To provide focusing, each camera employs a Tuneable Liquid Crystal Lens (TLCL). TLCL 34 is associated with camera 30, and TLCL 36 is associated with camera 32. TLCLs 34, 36 provide focus functionality for each of their respective cameras 30, 32.

TLCLs are known in the art. For example, TLCL structures are described in co-pending commonly assigned International Patent Application Serial No. PCT/CA2009/000742, filed Jun. 5, 2009, the entirety of which is incorporated herein by reference, and can be used for focusing images of a scene by changing the characteristics of a liquid crystal through which incident light from the scene passes. Without limiting the invention, TLCLs 34, 36 can be such structures.

As described in this and other disclosures, a TLCL is a liquid-crystal-based lens structure for which the optical power varies with changes in an applied electric field and not by physical movement of components. As the electric field is typically generated by an input electrical drive signal, varying the drive signal may be used to tune of the TLCL, for example to change the focus of the TLCL. For example, variable focus TLCLs are described in co-pending commonly assigned US 2009/0213321 A1 entitled "Tunable Liquid Lens With Reduced Aberration" filed Feb. 25, 2009, the entirety of which is incorporated herein by reference. The tuning range of such a TLCL may include a low optical power level which adds little focusing effect to an overall lens structure. Without limiting the invention, the low optical power may be zero. In accordance with an implementation, the TLCL is configured to provide infinity focus while employing the low/zero optical power. As the drive signal supplied to the TLCL 34, 36 is changed, the optical power of the TLCL changes, causing an overall change in focal length.

The use of TLCLs 34, 36 with cameras 30, 32 provides the desired focusing functionality without many of the drawbacks of the conventional mechanical focusing systems:

In particular FIGS. 6a and 6b illustrate, in accordance with a preferred embodiment of the proposed solution, a model of a miniature focusing system for a camera employing a pair of lenses including a variable focus TLC lens, TLC lens which is located at the aperture stop; and an image sensor at fixed distance from the lens structure. For certainty, the invention is not limited to a single TLC lens implementation. In accordance with the proposed solution, locating a variable focus TLC lens at the aperture stop advantageously eliminates the requirement for a telecentric lens.

FIG. 6a illustrates the ray diagram of such a variable focus system employing a TLCL at low optical power with an image sensor positioned to capture distant (effectively infinity) focus images. FIG. 6b illustrates the ray diagram of the same variable focus system having the same configuration illustrated in FIG. 6a, however with the TLCL at a positive optical power setting to capture close focus images. As seen from the ray diagrams, image magnification remains constant at all TLCL optical powers because the path of the chief ray is unchanged for all focus settings: falling at the same height on the image sensor located same distance (motion-less) away from the TLCL. In this sense, the physical TLCL having a typical thickness of 460 microns operates substantially like an idealized lens. According to the preferred embodiment of the proposed solution, such implementations greatly benefit from miniaturization and wafer scale manufacturing cost advantages compared to conventional focusing systems.

Additional benefits are derived from implementing such miniature focusing systems in dual camera systems for stereoscopic image capture. For example, focus synchronization of TLCLs 34, 36 is much easier since there are no mechanical movement settling delays and no ringing (momentum dissipation) phenomena:

With TLCLs 34, 36 having the advantage of being much smaller, compact and less expensive to produce than conventional mechanical optical systems, these aspects permit the fabrication of multiple TLCL in a combined monolithic structure. In accordance with an implementation of the preferred embodiment, TLCLs 34, 36 are fabricated on a single substrate, the monolithic arrangement representing a single focusing component 38 for the dual camera system. The size and cost advantages of the proposed solution are particularly important for compact and/or mobile device applications such as smart phones, portable computers, etc. which must be lightweight and must have low energy consumption. The invention is not limited to dual TLCL fabrication in a focusing component; a number of TLCLs may be fabricated monolithically in a stereoscopic focusing component to support particular applications in a very compact way to fit the footprint of corresponding devices. Multiple camera systems include, and are not limited to: engineering/manufacturing vision systems, home TV, home entertainment systems, game systems, motion capture systems, surveillance systems, etc.

Figure 7:
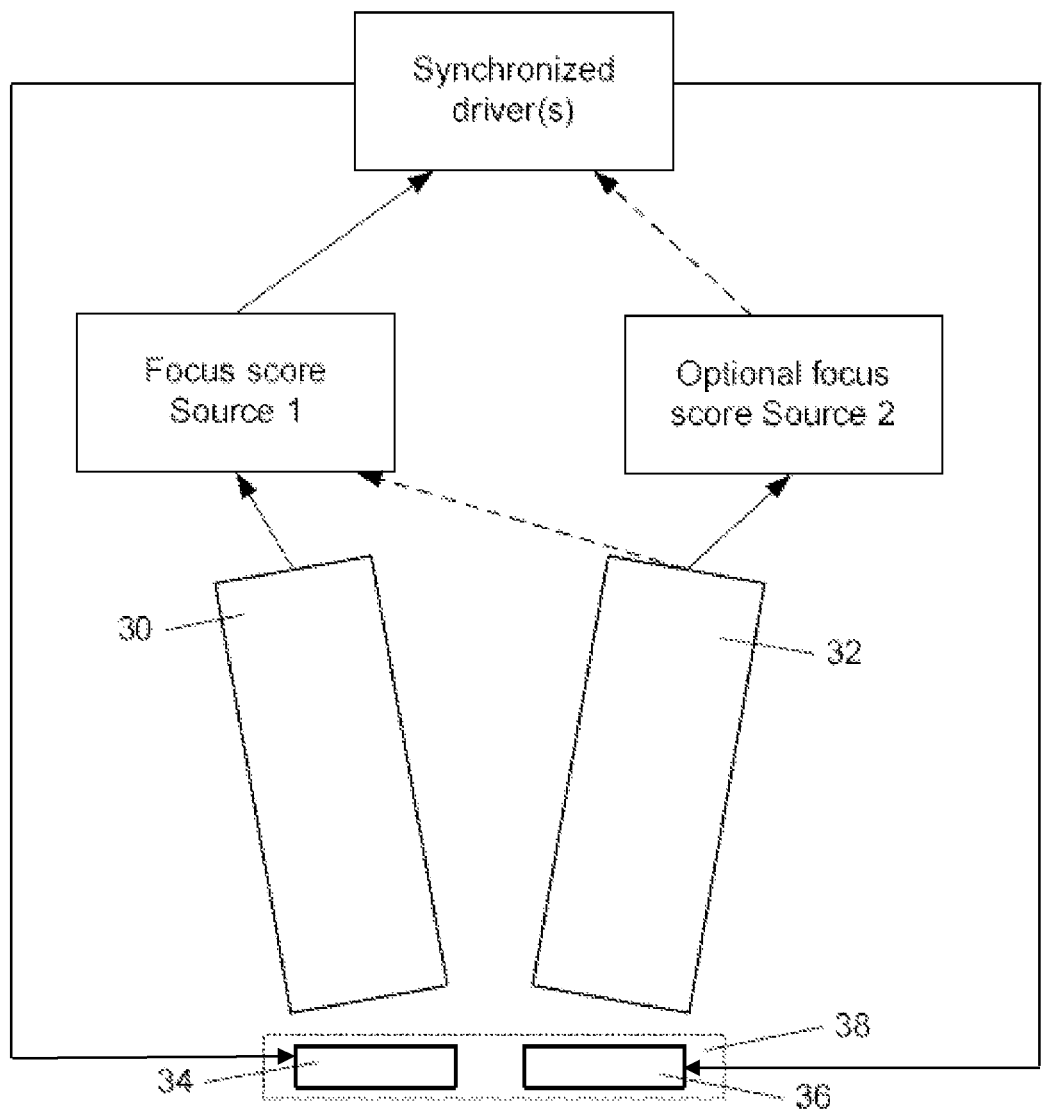
FIG. 7 is a schematic diagram showing an auto-focus dual camera system for capturing a three dimensional image of a scene in accordance with another embodiment of the proposed solution.

While multiple TLCL's may share a common fabrication structure, the TLCLs can be operated independently. In accordance with an embodiment of the proposed solution, FIG. 7 illustrates an auto-focus stereoscopic dual camera system for capturing 3D images of a scene. The dual camera system has a configuration much like that illustrated in FIG. 5. In accordance with the proposed solution, the monolithic focusing component is employed in conjunction with an auto-focus control system providing focus control for the camera pair. Cameras 30, 32 each have a respective TLCL 34, 36 used to focus each corresponding camera relative to the scene of interest.

Miniature TLCLs can also be fabricated monolithically and in a very compact way, for example to fit the footprint of a multi-camera device for applications such as but not limited to: endoscopic vision systems, general surgery vision systems, exploratory surgery systems, engineering vision systems, manufacturing inspection systems, etc.

Figure 8:
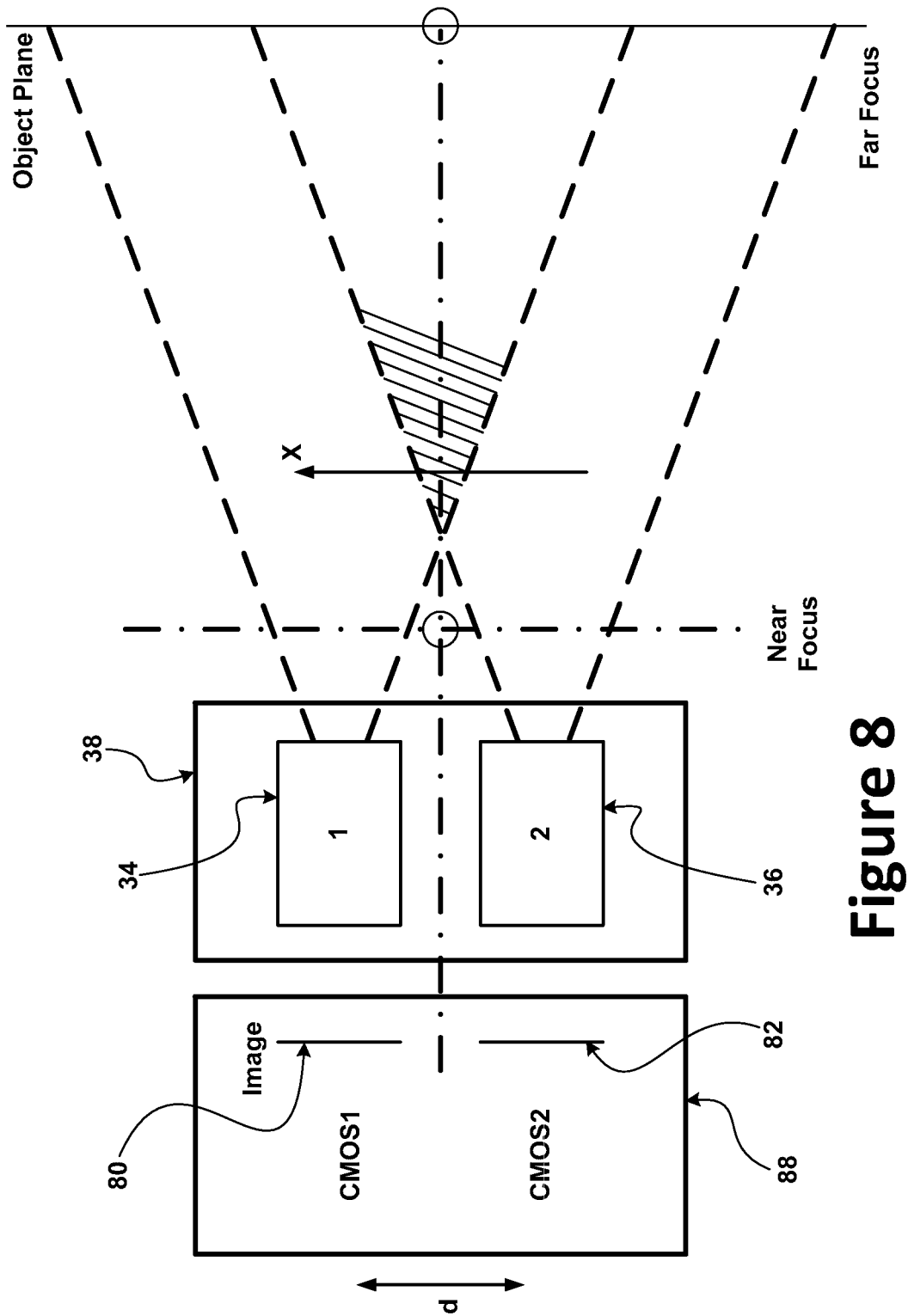
FIG. 8 is a schematic diagram showing a compact variable focus dual camera system for capturing three dimensional images of a scene in accordance with yet another embodiment of the proposed solution.

FIG. 8 illustrates a compact variable focus dual camera system for capturing three dimensional images of a scene of a micro world in accordance with yet another embodiment of the proposed solution. In accordance with an implementation of the embodiment, the cameras, represented by image sensors 80, 82 have a relative lateral shift d (pupil separation) however may not have a relative tilt angle a. Not only can the pair of TLCLs 34, 36 be fabricated as a monolithic image capture structure, the image sensors 80, 82 can also be fabricated as a common image capture component structure 88. Such miniature component structure has a small relative lateral shift d which provides a substantial overlap of two fields of view. The resulting different simultaneous laterally shifted views of the scene may provide a reasonable stereoscopic character for some applications. Without limiting the invention, the common image capture component structure can be fabricated employing wafer scale manufacturing. In some implementations, with appropriate micro spacers, complete camera modules can be wafer level fabricated.

Employing the combination of the monolithic image capture component 88 and the common focusing component 38 allows a high level of miniaturization enabling applications such as stereoscopic endoscopic camera systems, stereoscopic visual inspection systems, etc. For example, a stereo view of a micro world which looks similar to human natural stereo vision may be provided for Ma=1 and Z'inf=infinity. Assuming typical human vision to be described by stereo convergence distances from 200 mm to infinity for a baseline (lateral viewer's pupil separation) of 50 to 75 mm, the maximum scene angle=2 atan(75/400)=21°. For an application having as viewing requirements: stereo convergence distance=20 to 50 mm with a "Semi" field of view (FOV) of say 30°, natural stereoscopic mapping is provided by equating Viewing FOV=Acquisition FOV. At the closest distance of 20 mm and 21° convergence, the relative operational lateral shift d between camera pupils is given by 21°=2 atan(d/20) where d=3.75 mm. Accordingly, the world observable through such a system is the micro world scaled by Me in x, y and z.

Image Alignment

Comfortable 3D viewing depends upon careful alignment of the Left (L) and Right (R) images. The most important stereoscopic image alignment is up-down because human eyes cannot easily compensate for such misalignment errors. Even small up-down alignment errors can cause discomfort. Left-right alignment errors affect Z'inf perception, which can result in distorted Z (depth) reproduction nonlinearity. Extreme left-right misalignment may require the viewer's eyes to diverge to fuse images of distant objects, which is uncomfortable or impossible.

Image alignment can be performed in post processing after stereoscopic image acquisition, however such processing can be computationally inconvenient particularly for real time playback applications. If a 3D TV is the display means, it is simplest to critically align the two cameras, then use the full HDTV frame (for example) without shifting. This requires the two cameras to be aligned at manufacture which may introduce costly alignment procedures and alignment mechanisms.

Movable Optical Axis Liquid Crystal Lens

It has been discovered that the use of a movable optical axis liquid crystal lens on one or both cameras of a stereoscopic imaging system can provide: critical adjustment addressing Line of Sight (LOS) up-down and left-right alignment errors, without moving parts to register stereoscopic images of an object at infinity. As well it has been discovered that the 3D character of an imaged scene may be enhanced to some degree via differential left-right changes in the line of sight and differential focus changes. Moreover, the stereoscopic character of the implementation illustrated in FIG. 8 at close distances may be enhanced by TLCL tilt and/or shift which changes the optical axis of each channel (image sensor and lens system). Tunable Liquid Crystal Lenses having a movable optical axis are described in co-pending commonly assigned U.S. Provisional Patent Application 61/289,995 entitled "Image Stabilization And Shifting In A Liquid Crystal Lens" filed Dec. 10, 2009, the entirety of which is incorporated herein by reference.

Figure 9B:
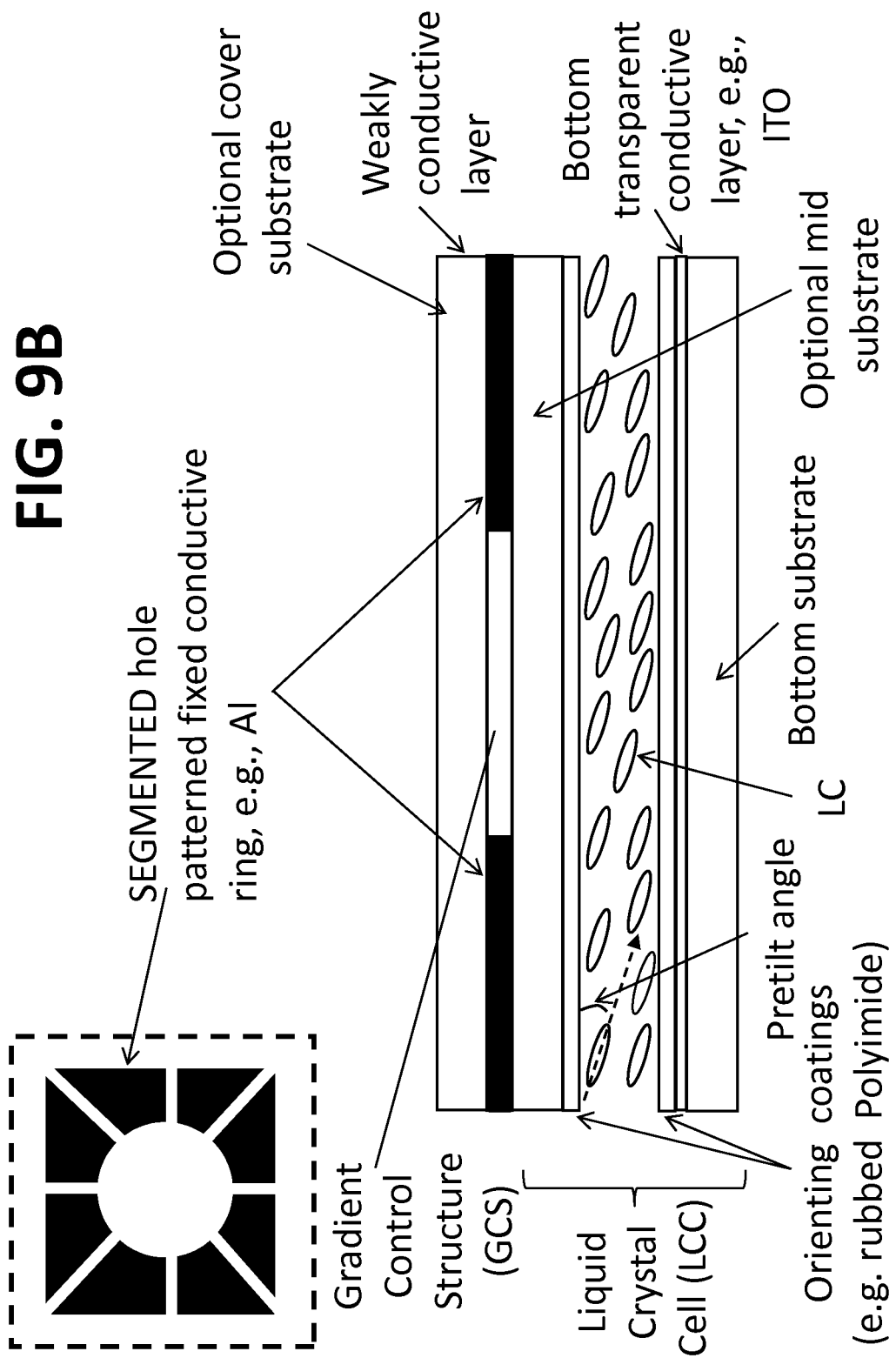
FIG. 9B is a schematic diagram showing a side sectional view of a tunable liquid crystal lens with an inset top view of a segmented top electrode according to an embodiment in which a frequency dependent material is within the aperture of the segmented, hole patterned electrode.

In accordance with the proposed solution, FIG. 9A illustrates a side sectional view of a tunable liquid crystal lens with an inset top view of a segmented top electrode according to an embodiment in which a frequency dependent material or a weakly conductive layer is above a segmented hole patterned electrode. It has been discovered that the optical axis of the lens can be moved by varying only the voltages of common frequency control signals fed to the segments. Alternatively, a change in the shape can be performed by varying the frequency of signals fed to the segments. The lens can be calibrated with a desired control signal frequency and amplitude for each segment as a function of optical power and of optical axis position, and a controller can draw on calibrated values from a look-up-table. Moreover, a controller may employ interpolation functionality to derive desired control signal frequencies and amplitudes based on calibrated values from the look-up-table.

Figure 9C:
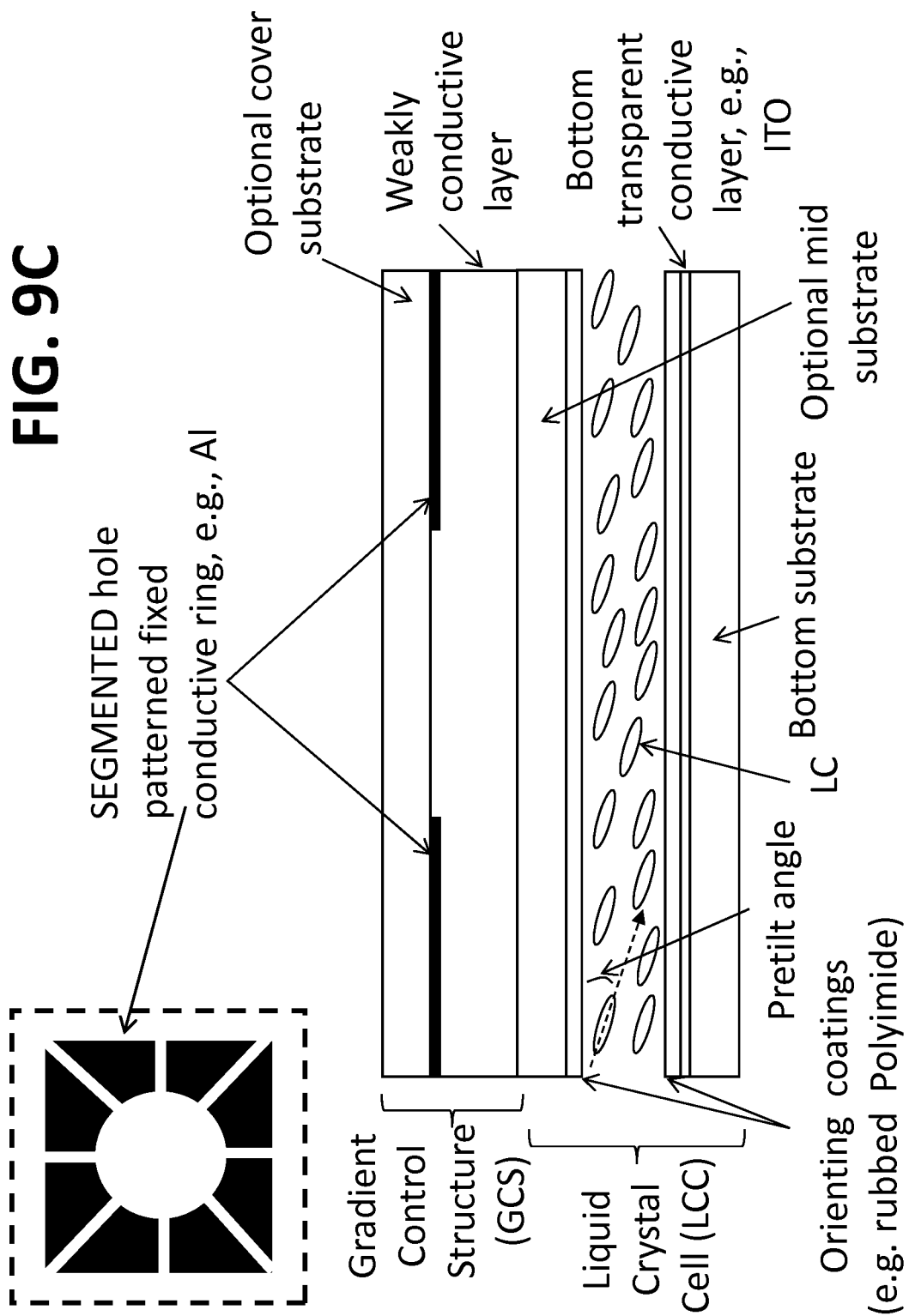
FIG. 9C is a schematic diagram showing a side sectional view of a tunable liquid crystal lens with an inset top view of a segmented top electrode according to an embodiment in which a frequency dependent material is below the segmented, hole patterned electrode.

The positioning of the frequency dependent material or weakly conductive layer can be on top of and covering the segmented electrode, within the aperture of the segmented electrode (see FIG. 9B) or below the segmented electrode (see FIG. 9C).

Figure 10A:
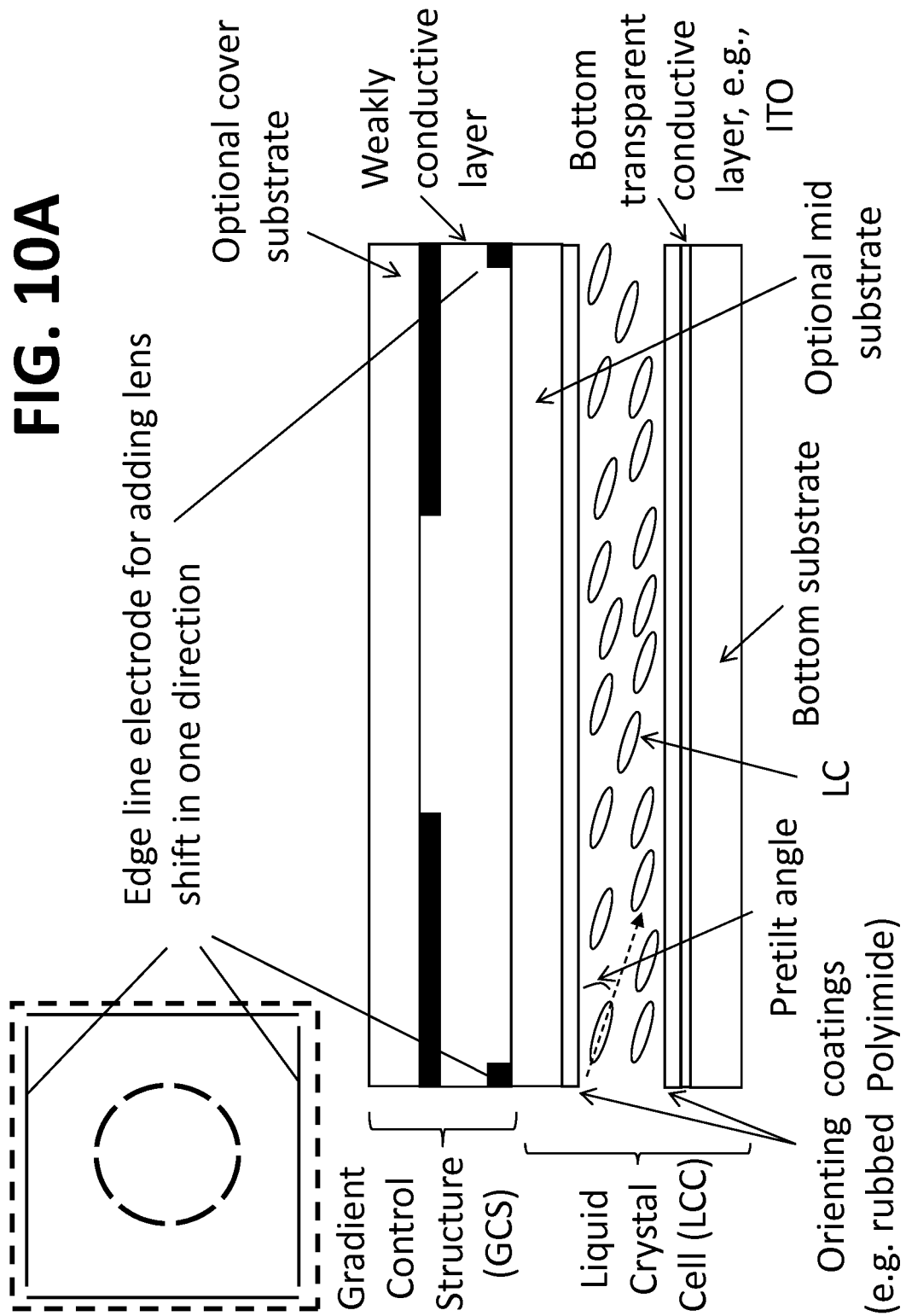
FIG. 10A is a schematic diagram showing a side sectional view of a tunable liquid crystal lens with an inset top view of a top, hole patterned electrode with additional lateral electrodes placed under the top hole patterned electrode according to an embodiment.
Figure 10B:
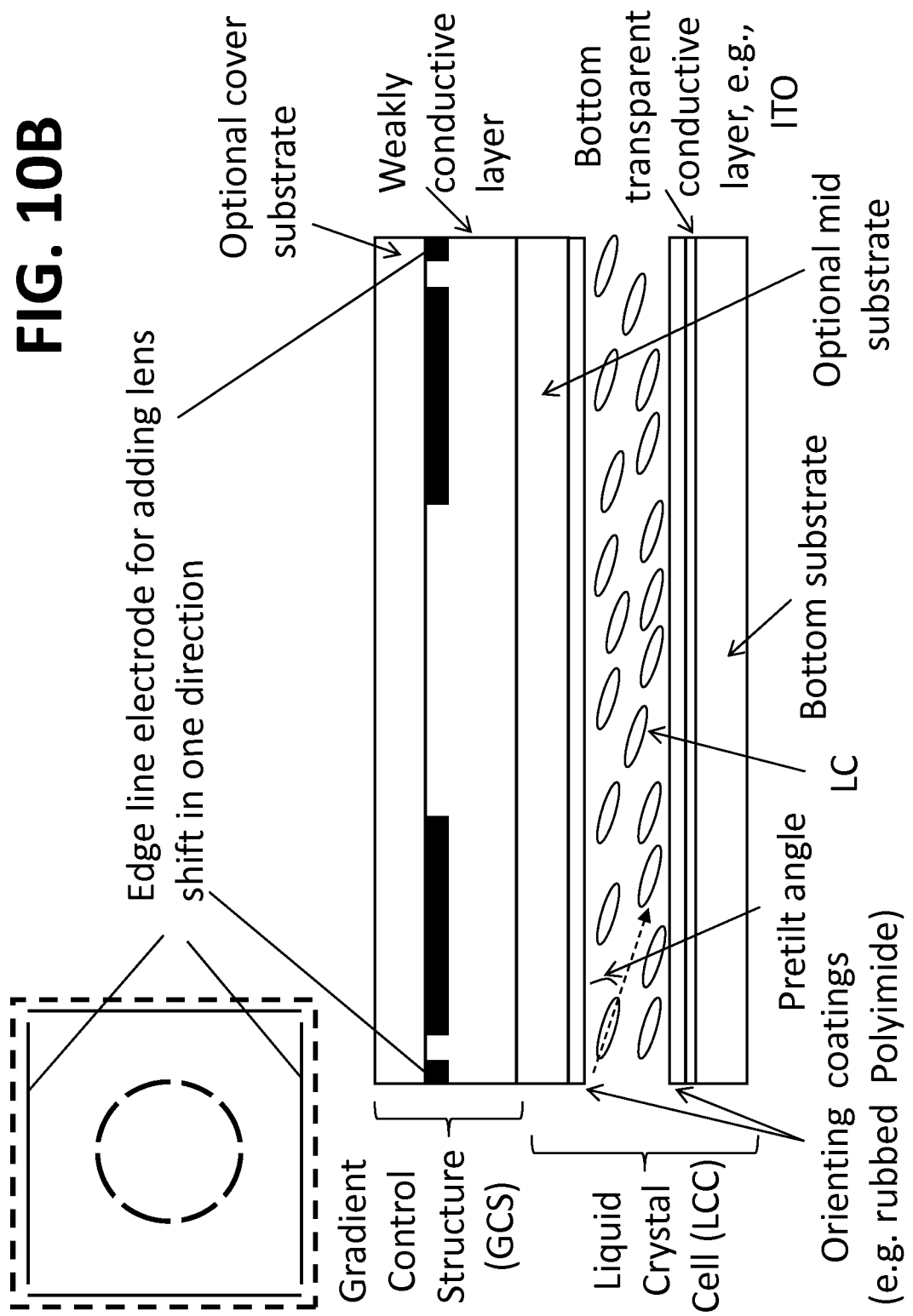
FIG. 10B is a schematic diagram showing a side sectional view of a tunable liquid crystal lens with an inset top view of a top, hole patterned electrode with additional lateral electrodes placed outside of periphery of the top hole patterned electrode according to another embodiment.

Altering the optical axis of the TLC lens by electric field shifting can be achieved without using a segmented electrode. For example, FIG. 10A illustrates a side sectional view of a tunable liquid crystal lens with an inset top view of a top, hole patterned electrode with additional lateral electrodes placed under the top hole patterned electrode. In this embodiment, a frequency is applied to a lateral or side electrode that increases the electric field across the liquid crystal cell in a decreasing manner from one side to the other. This type of control provides a type of beam steering or a type of incident ray angle selection that is combined with the lens formation. The side electrodes can be under the hole patterned electrode as illustrated or on a same substrate level outside of the periphery of the hole patterned electrode as illustrated in FIG. 10B.

Figure 11:
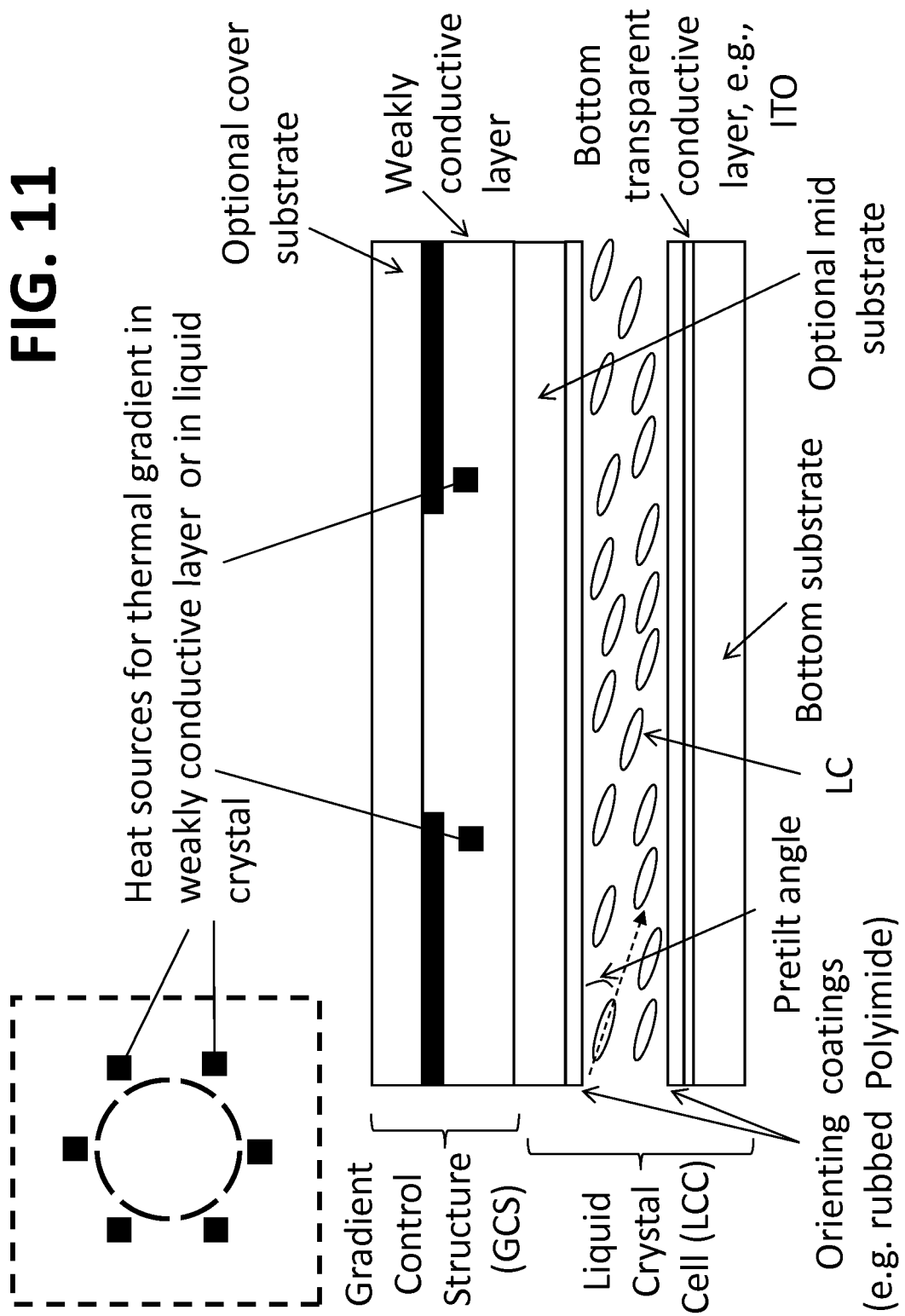
FIG. 11 is a schematic diagram showing a side sectional view of a tunable liquid crystal lens with an inset top view of a top, hole patterned electrode with additional resistive heat sources placed under the top hole patterned electrode according to a further embodiment.

The behavior of the frequency dependent material or weakly conductive layer can be affected by temperature. As illustrated in FIG. 11, the creation of a controllable thermal gradient within the frequency dependent material layer or within the weakly conductive layer can be used to move the optical axis of the lens and therefore reorient the optical axis of the image sensor and TLCL system. The temperature also affects the ability of the liquid crystal to change orientation, and thus this approach can be used within the liquid crystal layer as well. It will be appreciated that this technique for shifting the optical axis can be used with different arrangements for spatially modulating the liquid crystal orientation change, such as different techniques for spatially modulating the electric field or different techniques for spatially modulating the liquid crystal orientation, such as polymer dispersion or spatially programmed alignment layers.

Figure 12:
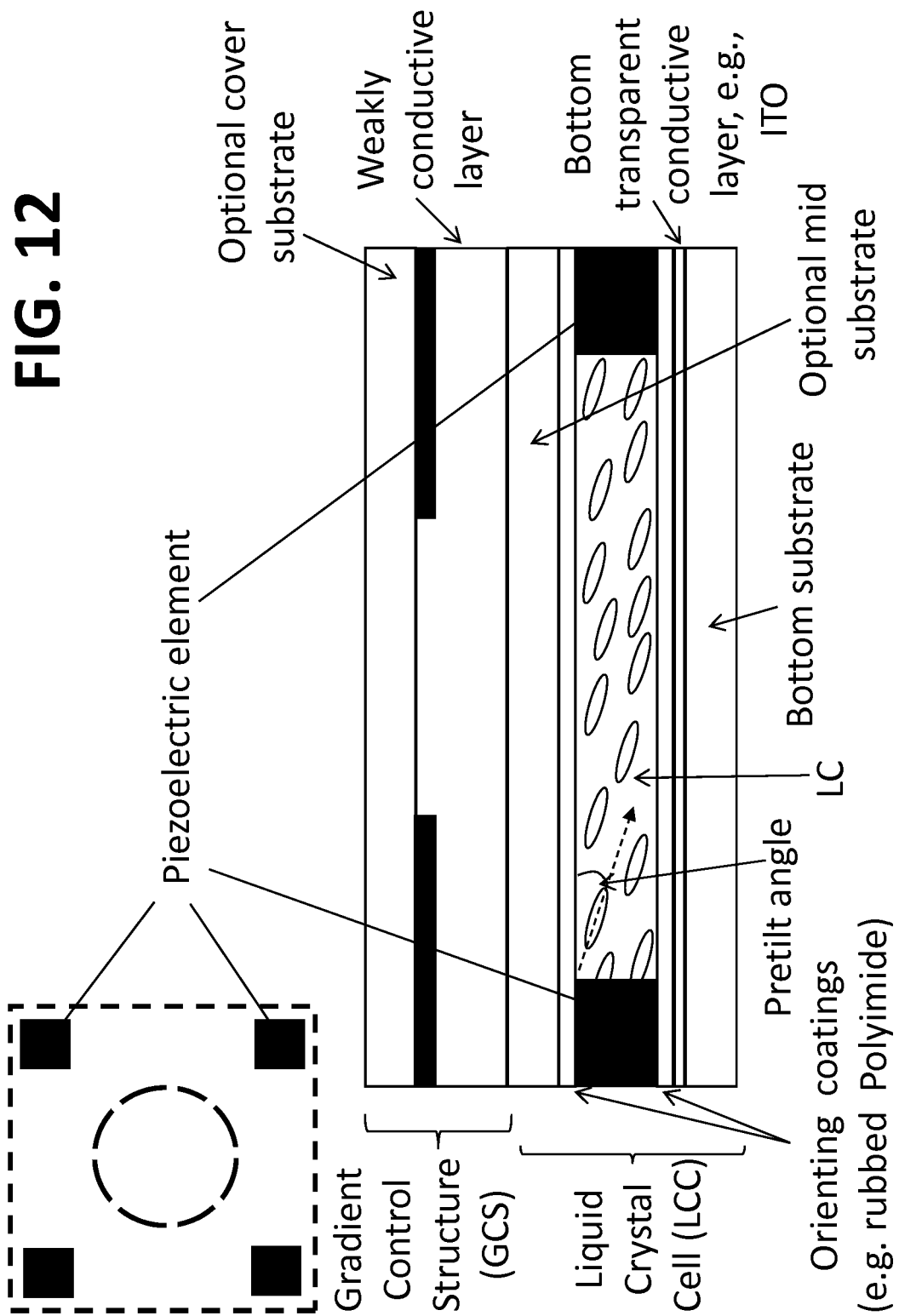
FIG. 12 is a schematic diagram showing a side sectional view of a tunable liquid crystal lens with an inset top view of a top, hole patterned electrode with additional piezoelectric elements placed between substrates of the liquid crystal cell in corners thereof according to yet another embodiment.

FIG. 12 illustrates a side sectional view of a tunable liquid crystal lens with an inset top view of a top, hole patterned electrode with additional piezoelectric elements placed between substrates of the liquid crystal cell in corners thereof which can be controllably driven electrically to expand and cause a desired tilt in the spacing between the substrates. Piezo elements can be deposited on the substrate during fabrication of the lens device. Alternatively, closed, fluid filled cells can be controllably heated to expand and cause the desired tilt in the spacing between the substrates. It will be appreciated that this technique for shifting the optical axis can be used with different arrangements for spatially modulating the liquid crystal orientation change, such as different techniques for spatially modulating the electric field or different techniques for spatially modulating the liquid crystal orientation, such as polymer dispersion or spatially programmed alignment layers.

Figure 13A:
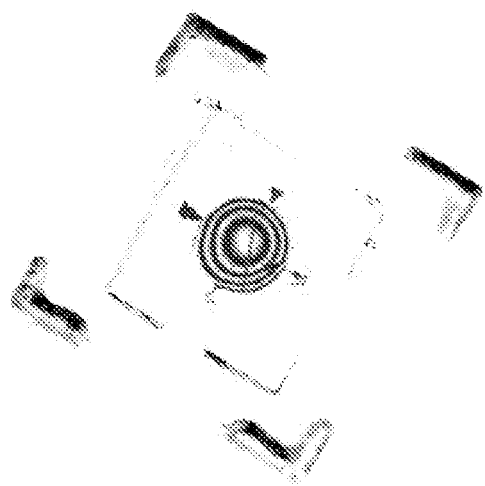
FIG. 13A is a schematic diagram showing a top view of a tunable liquid crystal lens of the embodiment of FIG. 9A, FIGS. 13B, 13C and 13D showing different states of shift of the tunable liquid crystal lens optical axis using the segmented electrodes.
Figure 13D:
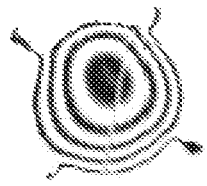
Figure 13C:
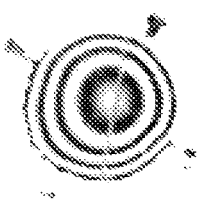
Figure 13B:
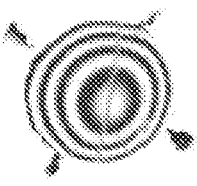

FIG. 13A illustrates a top view of a tunable liquid crystal lens of the embodiment of FIG. 9A with different states of shift 13B, 13C and 13D of the optical axis of the TLCL using the segmented electrodes. For certainty, movable optical axis liquid crystal lenses achieve shift and/or tilt without mechanical displacement. The ability of TLCLs having movable optical axes shift the images on the two image sensors providing changing Line(s) of Sight (LOS) without affecting the Points of View (POV) of the two cameras.

Movable Optical Axis Camera Module

In accordance with another embodiment of the proposed solution, image sensor tilt and/or shift with respect to a corresponding TLCL may be employed in order to alter the optical axis of an image sensor and TLCL camera module. Similarly, Piezo elements can be deposited on the substrate during fabrication of the image sensor. Alternatively, closed, fluid filled cells can be controllably heated to expand and cause the desired tilt in the spacing between the image sensor and TLCL. Reorienting the optical axis of the camera module via image sensor shift or tilt operates counter to optical axis reorientation via a corresponding TLCL shift or tilt.

While stereo convergence may be achieved by tilting TLCLs 34, 36 or by tilting image sensors 80, 82, such tilt induces keystone image distortions. Large keystone distortions may prevent image registration having a negative impact on the stereoscopic effect, while moderate keystone distortions may be distracting to a viewer. Employing dual camera systems to capture static scenes, moving objects, and object variations may require object tracking wherein both image channels employ optical axis reorientation. Tilting both optical axes would introduce keystone distortions in opposing directions further reducing image registration.

It has been discovered that shifting TLC lenses and/or image sensors provides stereo convergence superior to tilting TLC lenses and/or image sensors because shifting does not induce keystone image distortions.

Stereoscopic Effect Enhancement Via Purposeful Adjustment of Infinity Distance

It has been discovered that ability of movable optical axis TLCL to change LOS by shifting the images on the two image sensors can change the third 3D reproduction parameter Z'inf in a useful manner.

For example, a 3D stereoscopic imaging system is normally set up to capture a stereo scene between infinity and some close limit, where the infinite objects require zero convergence and near objects require positive convergence. It may be desirable (such as in macro stereoscopic image acquisition) to adjust convergence for closer objects, so that real infinity is actually divergent (and out of focus), while closer objects can be viewed comfortably.

FIG. 14a illustrates a model of a typical pair of cameras registered for infinite (D) plane left-right alignment, providing comfortable stereo image viewing from infinity to a finite distance, say 10 cm. If prisms are introduced (with an LVAF) that cause the cameras to register left-right image alignment in a plane 10 cm away from the cameras, as illustrated in FIG. 14b, a similar comfortable viewing is provided for objects in the scene 10 cm to 5 cm away (D) from the cameras. If the display was 1× (angular magnification), an object 10 cm away (D) would be perceived at infinity and an object 5 cm away (D) would seem to be at 10 cm. Objects more distant than 10 cm would be divergent, but 5 cm would be comfortably viewed. In addition the depth of field of the two cameras, if limited would need to match the object distance range (or the system should have focus adjustment ability). Such a mapping is illustrated in tabular form as follows:

| Mapping Table | |
|---|---|
| Object Distance: | Image Distance: |
| a) Original, infinity registered: | |
| Infinity | Infinity |
| 20 cm | 20 cm |
| 10 cm | 10 cm |
| b) 10 cm registered: | |
| 10 cm | Infinity |
| 6.667 cm | 20 cm |
| 5 cm | 10 cm |

Differential Focus Stereoscopic Effect Enhancement

In accordance with another embodiment of the proposed solution, a dual camera system (not shown) employs differently focused lenses at different magnifications however with good left-right registration. Such a dual camera system would provide a 3D image having a perceived increased scene depth without loss of stereo depth, or loss of viewing comfort.

Figure 14C:
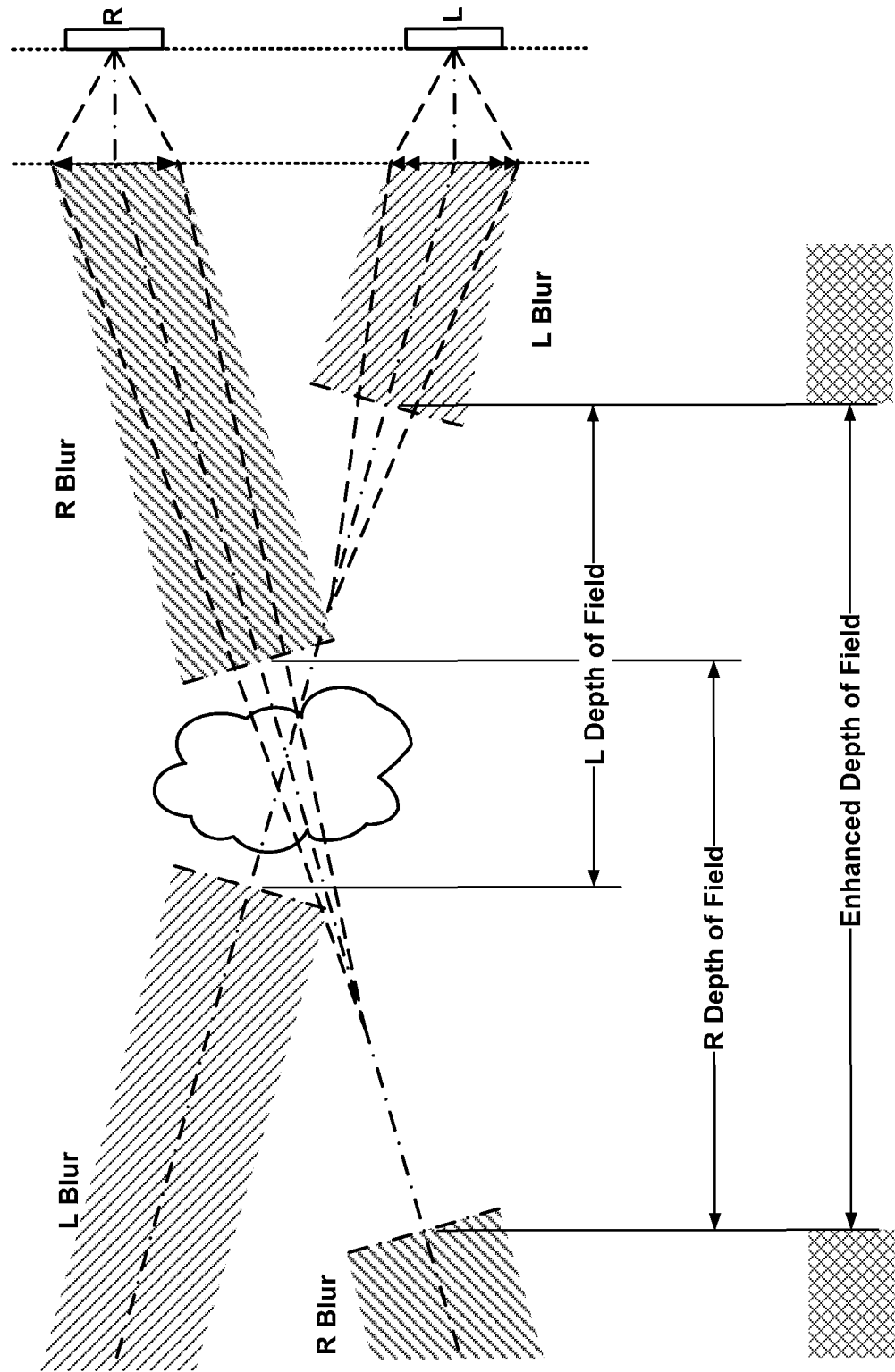

With reference to FIG. 14c, employing a constant magnification variable focus camera system, for example employing a TLCL at the aperture stop, depth of field may be set independently for each camera module while maintaining the imaged object in focus. With one camera is focused close so that the imaged object is close to the far limit of the corresponding depth of field range, while the other camera is focused far so that the same imaged object is close to the near limit of the corresponding depth of focus range, the perception of scene depth (mapping) would be preserved and the viewer would see details in both depth of field ranges and therefore the viewer would see details in an expanded (enhanced) depth of field range.

Method of Providing Stereoscopic Scene Depth

In accordance with the proposed solution, a method for stereoscopic image acquisition includes stereoscopic image registration followed by stereoscopic auto-focusing.

In accordance with an implementation of the proposed solution, stereoscopic image registration includes acquiring multiple sample images of a scene following the positioning of the overall stereoscopic imaging system in the vicinity of the scene substantially directed at the scene of interest. The sample images need not be of high quality as long as general features of the scene of interest can be distinguished. While scene focus would be desirable, only some optical power adjustment may be necessary to distinguish general features of the scene of interest. The process proceeds with attempting overlap of the multiple sample images. The invention is not limited to any particular method of image overlap, for example pattern matching may be employed. Such pattern matching functionality may provide at least one measure of feature displacement differences between the multiple images indicative of degrees of parallax. For example, each displacement difference may be expressed as a vector having a direction and a magnitude. Without limiting the invention, in a dual camera stereoscopic system one displacement difference can be sufficient. The stereoscopic image registration process employs the measure of displacement differences to determine an appropriate TLCL optical axis shift (and/or tilt) to improve registration in order to provide scene depth. The stereoscopic image registration process may be repeated to improve registration. As well, the stereoscopic image registration process may be performed continuously. Moreover, the stereoscopic image registration process may be performed in parallel with auto-focusing functionality (described below).

Figure 15:
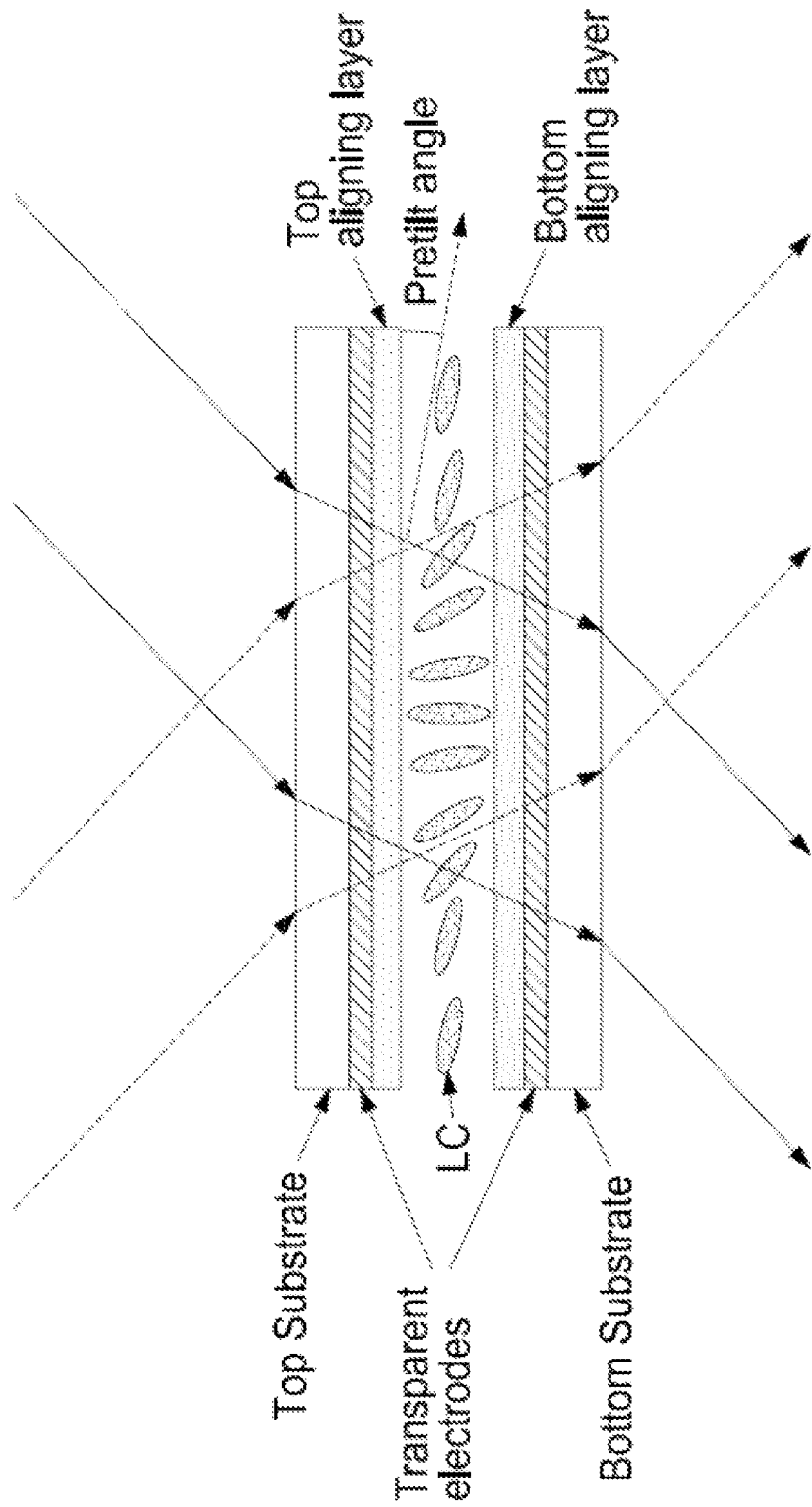
FIG. 15 is a schematic diagram showing an angular asymmetry of tunable liquid crystal lenses.
Figure 16B:
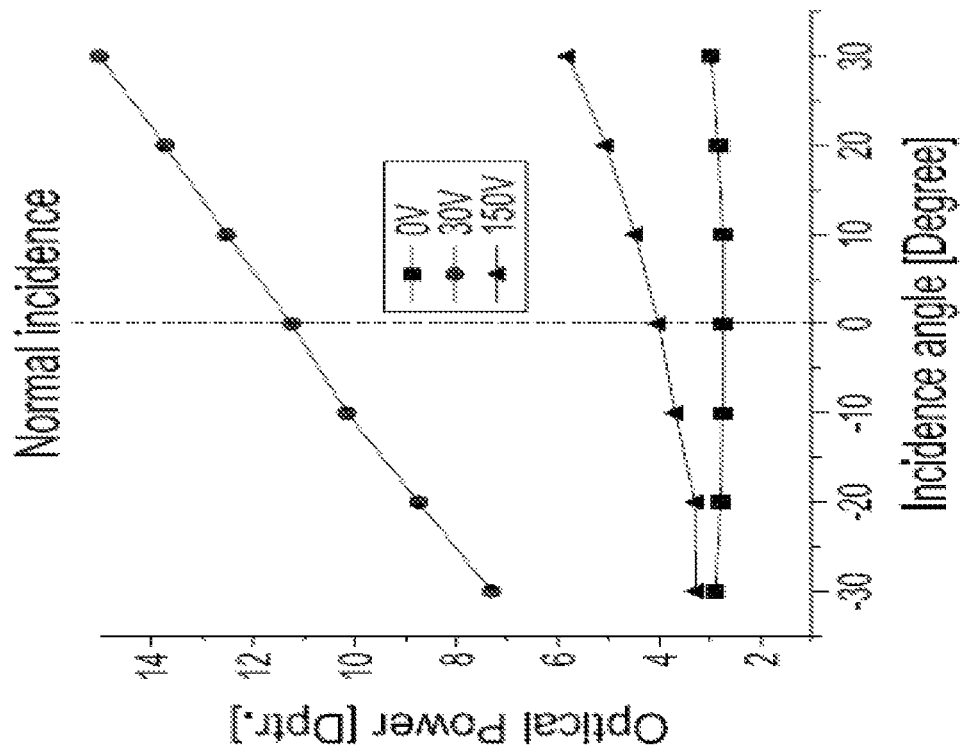
FIG. 16B is a plot illustrating experimental results showing an angular asymmetry for a standard tunable liquid crystal lens.
Figure 16A:
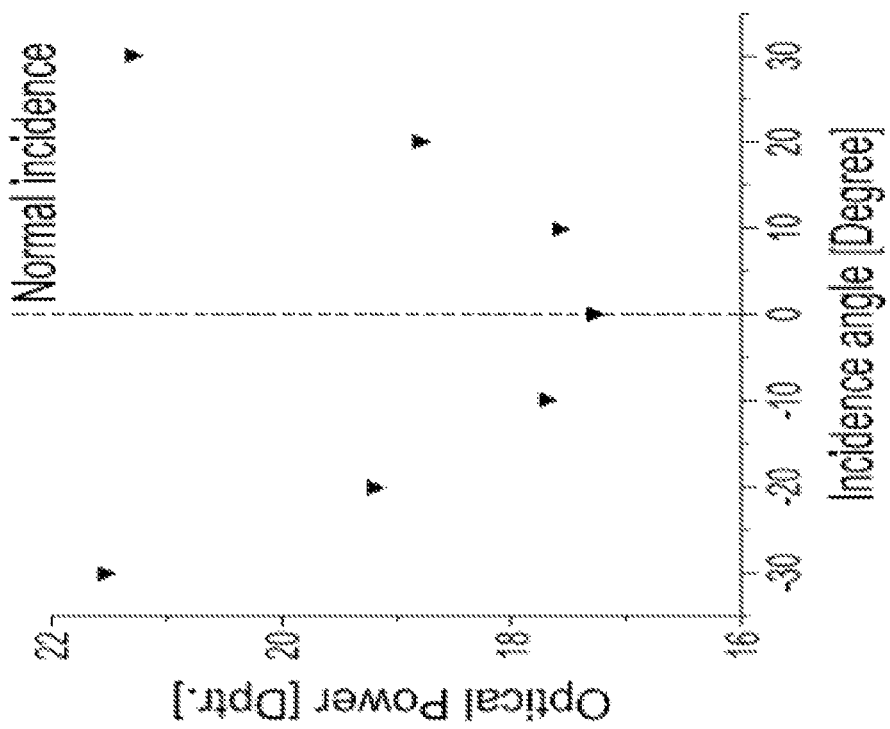
FIG. 16A is a plot illustrating experimental results showing an angular asymmetry for a standard achromatic lens (2.5 cm aperture, f1=17.54 Diopter, pupil diameter of Shack-Hartmann Wavefront sensor is 4 mm)

Eye tracking is known to be used to save computation time. In accordance with another implementation of the proposed solution, eye tracking information from an output component of a dual camera stereoscopic imaging system is employed in a modified stereoscopic image registration process to either guide and/or enhance pattern matching or to provide the measure of feature displacement difference between two images via eye convergence. In this sense, eye tracking information may be employed to provide triangulation. As TLCL shift (and/or tilt) is adjusted eye tracking information may provide feedback to limit the extent of shift (and/or tilt). Again, the eye tracking stereoscopic image registration process may be performed in parallel with auto-focusing functionality (described below). For certainty, while desirable, dual eye tracking is not an implied requirement. For example:

It has been discovered that a TLCL acting on two orthogonal polarizations can suffer the drawback that each half TLCL is sensitive to the angle at which rays interact with the liquid crystal as illustrated in FIGS. 15, 16A and 16B. The asymmetry shown, leads to a limited in-focus region of an image field of the TLCL. A TLCL having reduced sensitivity to the incident angle of light emanating from the scene of interest is described in co-pending commonly assigned PCT Patent Application PCT/CA/2009/000743, entitled "Tunable Liquid Crystal Optical Device", filed 2009 Jun. 5, which is incorporated herein by reference.

It has been discovered that by splitting a half TLCL into two opposite sign pre-tilt angle cells, even if controlled by the same electrode system, the optical properties of the half TLCL have much reduced angular dependence. It has also been discovered that two layers of liquid crystal can be arranged in a superposed manner with a mid layer separating the two layers, in which the upper layer has a top alignment layer and the lower layer has a bottom alignment layer with the mid layer not defining a pre-tilt angle within the liquid crystal layers. This arrangement allows the mid layer to be very thin and thus for the two liquid crystal layers to be controlled by essentially the same field, even when there is some gradual variation in the control field in the vertical direction within the liquid crystal layers. The two layers can have different zero field liquid crystal orientations defined by alignment layers, for example opposed pre-tilt angle layers, namely one layer providing a +alpha pre-tilt angle and a second layer with a −alpha pre-tilt angle. The mid layer can provide a direction of ordering of the liquid crystal at its surface without defining a pre-tilt angle, for example using with a stretched sheet of material. The liquid crystal can be given its orientation from the alignment layer of the top or bottom substrate and then this order is maintained by the mid layer having a direction of ordering.

Figure 17:
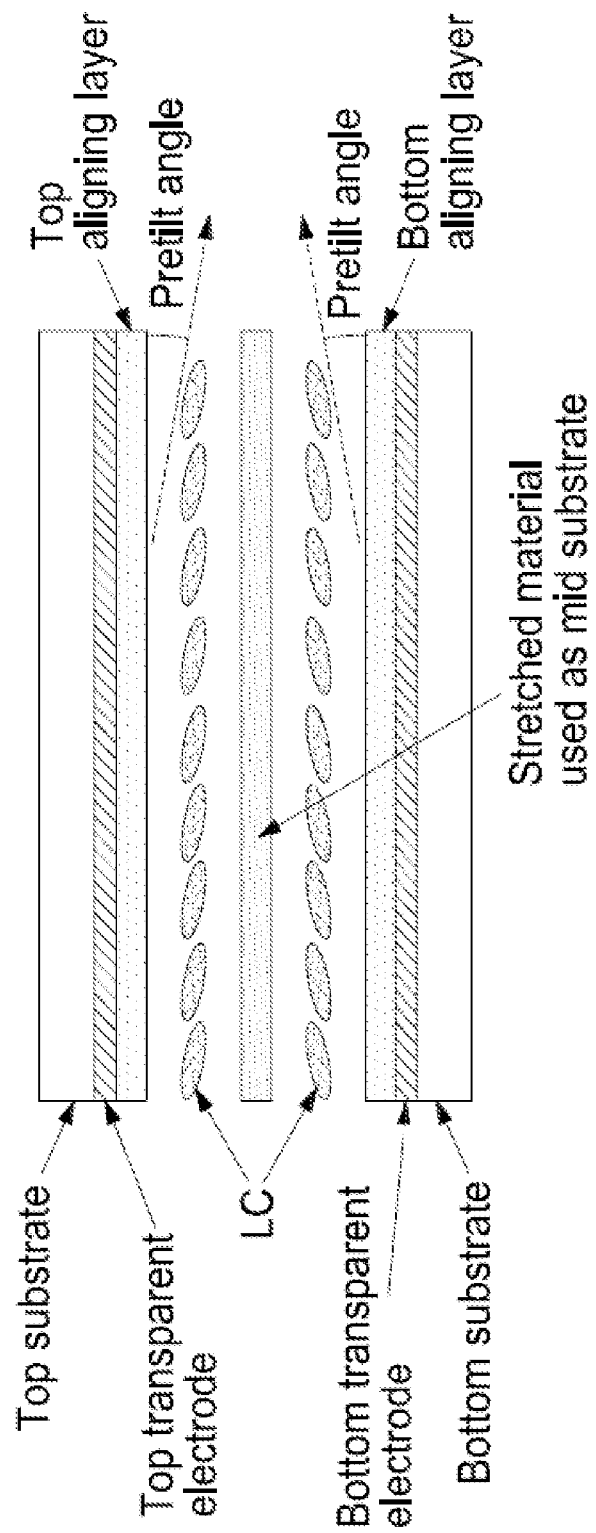
FIG. 17 is a schematic diagram showing a tunable liquid crystal lens structure in accordance with the proposed solution.

FIG. 17 illustrates such an embodiment in which the middle substrate is replaced by a stretched material. This reduces the thickness of the structure, thus improving electric field control. For example, a 20 micron thick polyimide can be suitable. Stretching of the polymer material (stretch marks) also creates a direction of the surface on the polymer that helps keep the liquid crystal oriented in the direction set out by the alignment layer. Stretching is a known technique of fabrication of anisotropic (or dichroic) polymer layers. When stretched in a given direction, many polymers can generate optical anisotropy. One of the mechanisms of such anisotropy is the alignment of molecular chains in the direction of stretching. When a liquid crystal is put in touch with a non stretched polymer surface, then there is no preferential direction of alignment. However, if the polymer is stretched and if it is composed of molecules which favor the parallel alignment of LC molecules, then the LC will be aligned in the stretched direction. Thus, without having a rubbed surface, a stretched material can help maintain order of LC molecules when the alignment layer is only on one surface of the LC cell. Of course, when the LC cell is thin, the influence of the single aligning layer can be sufficient if the mid substrate does not strongly attract the LC molecules in a different orientation. Such TLC lens provides an in-focus region of the image field having a wide extent.

In accordance with a further implementation of the proposed solution, employing a TLC lens with a wide in-focus region of the image field enables employing eye tracking to select a region of interest for image registration. Again, it is not necessary that both eyes in a dual camera stereoscopic system be tracked.

In accordance with yet another implementation of the proposed solution, eye tracking is employed to select a region in at least one image field on which the stereoscopic system is to focus. It is appreciated that such stereoscopic imaging systems can be employed with scenes having varying scene depths, and selecting the image field region for focus acquisition selects a (focus) depth of field at distance D away.

Stereoscopic Auto-Focus

Auto-focus algorithms for controlling a TLCL are described in co-pending commonly assigned WO 2010/022080 PCT Patent Application entitled "In-Flight Autofocus Method and System" claiming from Aug. 18, 2008, the entirety of which is incorporated herein by reference. In accordance with the proposed solution, dual camera implementation of FIG. 7 uses input signals such as focus scores to focus the multiple cameras onto the same scene in a synchronized manner, for example by using coupled capture and coupled auto-focus search algorithms. While focus scores provide a measure of sharpness of an image of the scene, the invention is not limited to employing focus scores, a variety of input signals may be employed as input to auto-focus algorithms. Without limiting the invention, focusing two or more cameras onto the same scene in a synchronized manner may include: combining multiple focus scores into a combined focus score employed by each TLCL 34, 36 to adjust focus; employing multiple focus scores based on a single auto focusing algorithm to drive each TLCL to adjust focus; employing multiple focus scores independently to adjust the focus of each TLCL; etc. Accordingly, such implementations provide a simultaneous focus search and a simultaneous auto-focus search convergence for multiple cameras.

For certainty, such a stereoscopic auto-focusing process is understood to be employed in conjunction (either in sequence or in parallel) with an image registration process such, but not limited to ones described above.

In accordance with the proposed solution, advantages are derived from: a low cost wafer fabrication; a rugged design having no mechanically movable parts; a monolithic focusing structure eliminating mechanical tolerances for focusing motion; improved auto-focus control eliminating ringing effects; improved multi-lens auto-focusing, monolithic object tracking in a scene, etc.

While the invention has been shown and described with referenced to preferred embodiments thereof, it will be recognized by those skilled in the art that various changes in form and detail may be made therein without departing from the spirit and scope of the invention as defined by the appended claims.

What is claimed is:

1. A stereoscopic imaging apparatus for capturing a stereoscopic image of a three dimensional scene, the apparatus comprising:
    a plurality of cameras;
    a focusing component including a variable optical power tunable liquid crystal lens corresponding to each camera of said plurality of cameras, said focusing component providing stereoscopic focus acquisition by focusing each liquid crystal lens on said scene at a scene distance away from said apparatus; and
    at least one of a pair of said tunable liquid crystal lenses including an optical axis orientation adjustment component providing a relative angle of view adjustment between said pair of liquid crystal lenses as a function of said scene distance.

2. An apparatus as claimed in claim 1, wherein each tunable liquid crystal lens comprises said optical axis orientation adjustment component.

3. An apparatus as claimed in claim 1, wherein each orientation adjustment component comprises at least one of: an optical axis tilt component, an optical axis shift component, a thermal gradient control system and a microactuator adjusting a spacing between substrates containing said liquid crystal of said lens.

4. An apparatus as claimed in claim 2, wherein each orientation adjustment component comprises at least one of: an optical axis tilt component, an optical axis shift component, a thermal gradient control system and a microactuator adjusting a spacing between substrates containing said liquid crystal of said lens.

5. An apparatus as claimed in claim 1, wherein each variable optical power tunable liquid crystal lens has electrical control characteristics, said apparatus further comprising a common tunable liquid crystal electrical control component for said at least two tunable liquid crystal lenses having matched electrical control characteristics.

6. An apparatus as claimed in claim 1, wherein each camera further comprises an image capture subsystem a fixed distance away from an aperture stop, said liquid crystal lens being located substantially at the aperture stop of said corresponding camera, said image capture subsystem being located at a fixed distance away from said aperture stop and said corresponding liquid crystal lens being located substantially at the aperture stop providing focus adjustment via tunable liquid crystal lens optical power adjustment at fixed magnification.

7. An apparatus as claimed in claim 1, said apparatus further comprising a common focus control component configured to provide said stereoscopic focus acquisition.

8. An apparatus as claimed in claim 1, wherein said focusing component further comprises said at least two tunable liquid crystal lenses fabricated as a single unit.

9. An apparatus as claimed in claim 1, wherein each tunable liquid crystal lens is manufactured employing semiconductor wafer fabrication, said focusing component further comprising said at least two tunable liquid crystal lenses fabricated on a single substrate.

10. An apparatus as claimed in claim 6, wherein each image capture subsystem further comprises an image sensor.

11. An apparatus as claimed in claim 6 further comprising a focus score source for each image capture subsystem configured to provide a focus score from information obtained from a corresponding image capture subsystem.

12. An apparatus as claimed in claim 1 said apparatus comprising one of an endoscope and a medical endoscope.

13. A stereoscopic imaging apparatus for capturing a stereoscopic image of a three dimensional scene, the apparatus comprising:
a plurality of cameras;
a focusing component including a variable optical power tunable liquid crystal lens corresponding to each camera of said plurality of cameras;
a common focus control component configured to provide stereoscopic focus acquisition by focusing each liquid crystal lens on said scene at a scene distance away from said apparatus: and
an optical axis orientation adjustment component associated with at least one of a pair of said tunable liquid crystal lenses, said optical axis orientation adjustment component providing a relative angle of view adjustment between said pair of liquid crystal lenses as a function of said scene distance.

14. An apparatus as claimed in claim 13, wherein each camera further comprises an image capture subsystem a fixed distance away from the aperture stop, said liquid crystal lens being located substantially at the aperture stop of said corresponding camera, said image capture subsystem being located at a fixed distance away from said aperture stop and said corresponding liquid crystal lens being located substantially at the aperture stop providing focus adjustment via tunable liquid crystal lens optical power adjustment at fixed magnification.

15. An apparatus as claimed in claim 13, wherein each tunable liquid crystal lens comprises said optical axis orientation adjustment component.

16. An apparatus as claimed in claim 13, wherein each orientation adjustment component comprises at least one of: an optical axis tilt component, an optical axis shift component, a thermal gradient control system and a microactuator adjusting a spacing between substrates containing said liquid crystal of said lens.

17. An apparatus as claimed in claim 15, wherein each orientation adjustment component comprises at least one of: an optical axis tilt component, an optical axis shift component, a thermal gradient control system and a microactuator adjusting a spacing between substrates containing said liquid crystal of said lens.

18. An apparatus as claimed in claim 13, wherein each variable optical power tunable liquid crystal lens has electrical control characteristics, said apparatus further comprising a common tunable liquid crystal electrical control component for said at least two tunable liquid crystal lenses having matched electrical control characteristics.

19. An apparatus as claimed in claim 13, wherein said focus control component further comprises said at least two tunable liquid crystal lenses fabricated as a single unit.

20. An apparatus as claimed in claim 13, wherein each tunable liquid crystal lens is manufactured employing semiconductor wafer fabrication, said focusing component further comprising said at least two tunable liquid crystal lenses fabricated on a single substrate.

21. An apparatus as claimed in claim 14, wherein each image capture subsystem further comprises an image sensor.

22. An apparatus as claimed in claim 14 further comprising a focus score source for each image capture subsystem configured to provide a focus score from information obtained from a corresponding image capture subsystem.

23. An apparatus as claimed in claim 13 said apparatus comprising one of an endoscope and a medical endoscope.

24. A method for acquiring a stereoscopic image employing an endoscope having a stereoscopic imaging system, the method comprising:
performing image registration between a plurality of acquired images by making a relative angle of view adjustment between a pair of liquid crystal lenses as a function of a scene distance, at least one of said pair of tunable liquid crystal lenses including an optical axis orientation adjustment component;
focusing multiple channels at said scene distance; and
acquiring a stereoscopic image set.

25. A method as claimed in claim 24 further comprising employing eye tracking to select a region of interest in at least one acquired image for image registration.

26. A method as claimed in claim 24 further comprising employing eye tracking to select a region of interest in at least one acquired image for focus acquisition.

27. A method as claimed in claim 24 further comprising employing differential focusing with overlapping depths of field to provide an enhanced depth of field.

28. A method as claimed in claim 24 further comprising scene depth mapping to provide an enhanced stereoscopic effect.

29. A method as claimed in claim 24 further comprising employing differential focusing with partially overlapping depths of field to provide an enhanced depth of field.

* * * * *